United States Patent
Li et al.

(10) Patent No.: US 12,378,295 B2
(45) Date of Patent: Aug. 5, 2025

(54) RATIONALLY DESIGNED PROTEIN COMPOSITIONS

(71) Applicants: 1GLOBE BIOMEDICAL CO., LTD., Beijing (CN); 1GLOBE HEALTH INSTITUTE LLC, Norwood, MA (US)

(72) Inventors: Chiang J. Li, Cambridge, MA (US); Shyam Unniraman, Newton, MA (US); Hannah Bader, Waltham, MA (US); Alan Lau, Malden, MA (US)

(73) Assignees: 1GLOBE BIOMEDICAL CO., LTD., Beijing (CN); 1GLOBE HEALTH INSTITUTE LLC, Norwood, MA (US)

( * ) Notice: Subject to any disclaimer, the term of this patent is extended or adjusted under 35 U.S.C. 154(b) by 1043 days.

(21) Appl. No.: 17/288,273

(22) PCT Filed: Oct. 29, 2019

(86) PCT No.: PCT/CN2019/114026
§ 371 (c)(1),
(2) Date: Apr. 23, 2021

(87) PCT Pub. No.: WO2020/088459
PCT Pub. Date: May 7, 2020

(65) Prior Publication Data
US 2021/0388049 A1 Dec. 16, 2021

Related U.S. Application Data

(60) Provisional application No. 62/811,116, filed on Feb. 27, 2019, provisional application No. 62/752,293, filed on Oct. 29, 2018.

(51) Int. Cl.
C07K 14/55 (2006.01)
C07K 16/28 (2006.01)
A61K 38/00 (2006.01)
A61K 39/00 (2006.01)

(52) U.S. Cl.
CPC .......... *C07K 14/55* (2013.01); *C07K 16/2827* (2013.01); *A61K 38/00* (2013.01); *A61K 2039/505* (2013.01); *C07K 2317/41* (2013.01); *C07K 2317/622* (2013.01); *C07K 2317/732* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| 5,877,293 A | 3/1999 | Adair et al. |
| 5,886,152 A | 3/1999 | Nakatani et al. |
| 6,054,297 A | 4/2000 | Carter et al. |
| 6,696,245 B2 | 2/2004 | Winter et al. |
| 6,846,634 B1 | 1/2005 | Tomlinson et al. |
| 2004/0202995 A1 | 10/2004 | de Wildt et al. |

FOREIGN PATENT DOCUMENTS

| CN | 107915777 A | 4/2018 |
| EP | 2639241 A2 | 9/2013 |
| WO | 2012107417 A1 | 8/2012 |
| WO | 2017220989 A1 | 12/2017 |
| WO | 2018184964 A1 | 10/2018 |
| WO | WO2018184965 A1 | 10/2018 |

OTHER PUBLICATIONS

Chen et al., Therapeutic efficacy of an anti-PD-L1 antibody based immunocytokine in a metastatic mouse model of colorectal cancer; 2016, Biochemical and Biophysical Research Communications, 480:160-165. (Year: 2016).*
Written Opinion of the International Searching Authority issued in the parent PCT application PCT/CN2019/114026, mailed on Feb. 6, 2020.
Baron et al., "Co-regulation of two gene activities by tetracycline via a bidirectional promoter," Nucleic Acids Res. 1995, 23:3605-3606.
Bird et al., "Single Chain Antigen-binding Proteins," Science 1988, 242:423-426.
Bowie et al., "A Method to Identify Protein Sequences That Fold into a Known Three-Dimensional Structure," Science 1991, 253:164-170.
Connell, N. D. "Expression systems for use in actinomycetes and related organisms," Curr. Opin. Biotechnol. 2001 12(5):446-9.
Goeddel, D. V. "Systems for Heterologous Gene Expression," Gene Expression Technology: Methods in Enzymology, 1990, 185:3-7 (Academic Press, San Diego, Calif).
Holliger et al., "'Diabodies': Small bivalent and bispecific antibody fragments," Proc. Natl. Acad. Sci. USA, 1993, 90:6444-48.
Honegger and Pluckthun, "Yet Another Numbering Scheme for Immunoglobulin Variable Domains: An Automatic Modeling and Analysis Tool," J. Mol. Biol, 2001, 309(3):657-670.
Huston et al., "Protein engineering of antibody binding sites: Recovery of specific activity in an anti-digoxin single-chain Fv analogue produced in *Escherichia coli*," Proc. Natl. Acad. Sci. USA, 1988, 85 : 5879-83.
Lefranc et al., "IMGT unique numbering for immunoglobulin and T cell receptor constant domains and Ig superfamily C-like domains," Dev. Comp. Immunol., 2005, 29:185-203.
Makrides, S. C. "Strategies for Achieving High-Level Expression of Genes in *E. coli*," Microbiol. Rev. 1996, 60(3):512-38.
Mayfield et al., "Expression and assembly of a fully active antibody in algae," Proc. Natl. Acad. Sci. USA. 2003, 100(2):438-42.
Poljak, R. J. "Production and structure of diabodies," Structure, 1994, 2:1121-23.

(Continued)

*Primary Examiner* — Daniel E Kolker
*Assistant Examiner* — James Ryland Melchior
(74) *Attorney, Agent, or Firm* — Milstein Zhang & Wu LLC; Duan Wu, Esq.

(57) ABSTRACT

Novel compositions and methods relating to or derived from a rationally designed fusion protein composition combines a therapeutic antibody with an IL2 mutant that can simultaneously enhance anti-tumor immunity or derepress tumor-associated immunosuppression along with direct activation of effector cells by IL2 without activating $T_{reg}$ are provided. The fusion protein can be used to prevent or therapeutically treat cancer.

14 Claims, 10 Drawing Sheets
Specification includes a Sequence Listing.

(56) References Cited

OTHER PUBLICATIONS

Raju et al., "Glycoengineering of Therapeutic Glycoproteins: In Vitro Galactosylation and Sialyation of Glycoproteins with Terminal N-Acetylglucosamine and Galactose Residues," Biochemistry, 2001, 40:8868-76.
Sharp and Cowe, "Synonymous Codon Usage in S. cerevisiae," Yeast, 1991, 7:657-78.
Sinclair and Choy, "Synonymous codon usage bias and the expression of human glucocerebrosidase in the methylotrophic yeast, Pichia pastoris," Protein Expr. Purif., 2002, 26:96-105.
Ward, E. S. et al., "Binding activities of a repertoire of single immunoglobulin variable domains secreted from *E. coli*," Nature, 1989, 341:544-546.
Hutmacher, C. et al.: "Antibody—cytokine fusion proteins: Biopharmaceuticals with immunomodulatory properties for cancer therapy", Adv Drug Delivery Rev, 141 (2019) 67-91.
EPO, extended European search report in corresponding EP Application No. 19878076.9 mailed Nov. 25, 2022.
JPO, first official action in corresponding Japanese Patent Application No. 2021-547634, including search result, mailed Sep. 19, 2023.
IP Australia, Examination report No. 1 in corresponding Australian Patent Application No. 2019371994, mailed Feb. 15, 2024.
CIPO, first official action in corresponding Canadian Patent Appln No. 3117853, mailed Apr. 5, 2024.
CNIPA, search report in corresponding Chinses applictaion No. 201980071932.6, mailed Jun. 7, 2023.
FIPS, First Office action and search report in corresoponding Russian Patent Application No. 202111229810, mailed Mar. 27, 2023.
Taiwan IP Bureau, first office action in corresponding Taiwan Patent application No. 108139140, mailed Aug. 18, 2023.
IPOS, first Wirtten Opinion in corresponding Singapore Patent Application No. 11202104297X, mailed Dec. 29, 2022.

\* cited by examiner

RATIONALLY DESIGNED PROTEIN COMPOSITIONS

CROSS-REFERENCE TO RELATED APPLICATIONS

This application is a national phase application under 35 U.S.C. 371 of the international application PCT/CN2019/114026, filed Oct. 29, 2019 which, in turn, claims priority to and the benefit of U.S. provisional patent application Ser. Nos. 62/752,293 filed Oct. 29, 2018, and 62/811,116 filed Feb. 27, 2019, which applications are incorporated herein by reference in entirety.

BACKGROUND OF INVENTION

IL2

Interleukin-2 (IL2) is a cytokine that plays a central role in both the resting and activated states of the immune system. During the resting stage, IL2 primarily ensures the development and survival of CD4+ Foxp3+ regulatory T-cells ($T_{reg}$s). However during an immune response, it promotes the proliferation and expansion of effector and memory T-cells and natural killer (NK) cells. It also enhances the effector function of these cells. IL2 is secreted by a variety of cells upon activation (CD8+ T-cells, NK and NKT-cells, DCs, and mast cells) but most of it comes from CD4+ T-cells; and it can work in an autocrine or paracrine manner.

Three polypeptide chains are involved in making up the IL2 receptor which bind to IL2 with different affinities when present in various combinations (Table 1). The biologically important versions of the receptor can be differentiated by their affinity for IL2: the low affinity (CD25 alone), intermediate affinity ($\beta\gamma$) and high affinity ($\alpha\beta\gamma$). CD122 and the common $\gamma$ chain are necessary for signaling upon IL2 binding, while CD25 increases receptor affinity but does not appear to signal.

TABLE 1

IL2 receptors based on the combination of subunits

| Subunit | IL2 binding (Kd) | IL2 signals |
|---|---|---|
| CD25 ($\alpha$) (Low affinity) | $10^{-8}$M | – |
| CD122 ($\beta$) | $10^{-7}$M | – |
| $\gamma$ (Common $\gamma$ chain) | Not detectable | – |
| $\alpha\beta$ | $10^{-10}$M | – |
| $\alpha\gamma$ | $10^{-8}$M | – |
| $\beta\gamma$ (Intermediate affinity) | $10^{-9}$M | + |
| $\alpha\beta\gamma$ (High affinity) | $10^{-11}$M | + |

The diverse functions of IL2 are largely a result of the differential expression of various IL2 receptor subunits on different cell types. On resting immune cells, CD25 is mainly confined to $T_{reg}$s, which also express the other IL2 receptor subunits, thus making them the primary target of low level IL2 in the resting state. On effector T cells, CD25 is upregulated on recently activated T-cells, along with a small increase in CD levels while the common $\gamma$ chain expression is relatively constant, resulting in increased sensitivity and high dependence on IL2 during the expansion phase. During later stages of an immune response, memory CD8+ T-cells and NK cells express very high levels of CD122 along with the $\gamma$ chain allowing them to compete with $T_{reg}$s for IL2.

Given IL2's role as a general T-cell growth factor, it has been used in clinics for several decades as a cancer immunotherapy. However, given the pattern of expression of the receptors, a high dose of IL2 is needed to activate intermediate-affinity receptor-bearing effector T and NK cells sufficiently to counteract its actions on the high-affinity receptor-bearing $T_{reg}$ cells. Another problem with IL2 administration is that it has a half-life of less than 30 minutes in blood and therefore needs to be continuously infused or repeatedly injected to sustain a high enough titer to have a therapeutic effect. The high dose regimen results in many side effects including pulmonary edema (due to CD25 expression in pulmonary epithelial cells), hypotension, vascular leak syndrome, etc. Furthermore, the expansion of $T_{reg}$ cells in the patients poses a continued threat against the anti-tumor response.

To circumvent these limitations of IL2 therapy, chemical modification, e.g. PEGylation has been used to reduce or alter the receptor selectivity of IL2 and to increase its half-life. Another approach was to use a specific anti-IL2 antibody to form a complex with IL2 to achieve preferential targeting of CD122-expressing cells. However, both these approaches have so far met with limited clinical success in addition to manufacture challenges. Alternatively, there are mutants of IL2 that preferentially bind CD122, or no longer bind CD25, allowing the effector T cells to better compete with $T_{reg}$ cells for IL2. However these molecules continue to have a short half-life like wild type IL2, therefore requiring repeated infusions.

Checkpoint Antibodies

Under normal physiological conditions, immune checkpoints are molecular pathways that have evolved for the maintenance of self-tolerance and to protect tissues from damage when the immune system is responding to infections. Tumors co-opt these pathways by mis-expressing immune-checkpoint proteins, generating an immune-suppressive environment and evading the immune system. Over the past decade, antibodies that block the CTLA-4 and PD1/PDL1 pathways have been shown to reverse tumor-associated immunosuppression and have proved to be highly successful in the clinic. However, despite their promise, these antibodies only work on a small fraction of patients for reasons that are not completely clear yet. As a result, there is a need for a better understanding of predictive biomarkers and therapeutics that can be used in combination with checkpoint antibodies.

BRIEF SUMMARY OF THE INVENTION

The present invention meets the above challenges by using rationally designed fusion protein compositions that can simultaneously enhance anti-tumor immunity or derepress tumor-associated immunosuppression along with direct activation of effector cells by IL2 without activating $T_{reg}$. The fusion proteins of the present invention comprise a portion of or an entire immune checkpoint antibody, and a mutant Interleukin-2 (IL2) polypeptide. The fusion proteins of the present invention can be used to treat tumors as monotherapies or in combination with (a) antibodies targeting at least another immunosuppressive pathway; (b) chemotherapy, targeted therapy or radiation therapy; (c) another mechanism of blocking an immunosuppressive pathway, e.g., aptamers or RNAi; or (d) another immunotherapy agent, e.g. a cytokine, a targeted therapeutic, etc.

In one aspect, the present invention provides a fusion protein that combines an immune checkpoint antibody (also called anti-checkpoint antibody or anti-CP antibody hereinafter) with an IL2 mutant that is less selective towards the high affinity receptor (or interchangeably, an intermediate-affinity receptor selective mutant, MutIL2). The fusion protein is comprised of a complete anti-CP antibody connected to MutIL2 on the C-terminal end of the heavy chain (FIG. 1A). This approach would add a linker sequence between the C-terminal end of the heavy chain and MutIL2. In addition, the presence of the Fc portion of the antibody allows for the use of the Fc neonate receptor pathway to enhance the half-life of the fusion protein by orders of magnitude. Moreover, the presence of a tumor-targeting antibody will help deliver IL2 preferentially into the tumor and reduce systemic side effects.

In one feature, the anti-CP antibody is an anti-PDL1 antibody. Preferably, the anti-PDL1 antibody has one or more of the following features that can increase the anti-tumor capability of the fusion protein: (a) it binds PDL1 with Kd<100 nM to purified protein as well as protein-expressed on the cell surface; (b) it blocks PDL1-PD1 interaction in vitro; and (c) it de-represses PDL1-mediated repression of effector T cells in activated PBMC cultures.

In one embodiment, the anti-PDL1 antibody is an antibody of any available isotype or any known mutant forms of the Fc region that inactivates, reduces or enhances ADCC and/or CDC functions. In a preferred embodiment, the anti-PDLL antibody is an antibody of IgG1 isotype. In some embodiments, the anti-PDLL antibody includes a pair of heavy chain variable region and light chain variable region where their respective sequences consist essentially of the following: (a) SEQ ID NO: 3 and SEQ ID NO: 6; (b) SEQ ID NO: 9 and SEQ ID NO: 12; or (c) SEQ ID NO: 15 and SEQ ID NO: 18. In some embodiments, the anti-PDL1 antibody further includes a second pair of heavy and light chains variable regions substantially identical to those of the first pair. In other embodiments, the anti-PDLL antibody includes a pair of heavy chain and light chain where their respective sequences consist essentially of the following: (a) SEQ ID NO: 2 and SEQ ID NO: 5; (b) SEQ ID NO: 8 and SEQ ID NO: 11; or (c) SEQ ID NO: 14 and SEQ ID NO: 17.

In one feature, the MutIL2 has one or both of the following features that can increase the anti-tumor capability of the fusion protein: (a) reduce ability to activate CTLL2 and human and mouse $T_{reg}$ while retaining its ability to activate effector T cells or NK cells; and (b) a up to 10-fold to over 1000-fold increase in its relative ability to activate $T_{eff}/T_{reg}$ compared to wild type IL2. In a further embodiment, the MutIL2 includes amino acid sequences substantially identical to the amino acid sequences selected from the group consisting of SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57 and combinations thereof.

In one feature, the linker sequence is a flexible serine-glycine linker or other known variants or linkers. In one embodiment, the linker sequence is SEQ ID NO: 19.

In one feature, the fusion protein comprising: an antigen binding part comprising a portion of or an entire anti-PDL1 antibody and a mutant Interleukin-2 (IL2) polypeptide, the antigen binding part includes a pair of heavy chain and light chain where their respective sequences consist essentially of the following: (a) SEQ ID NO: 2 and SEQ ID NO: 5; (b) SEQ ID NO: 8 and SEQ ID NO: 11; the mutant IL2 polypeptide includes amino acid sequence substantially identical to an amino acid sequence selected from the group consisting of SEQ ID NO: 25, SEQ ID NO: 27; and the mutant IL2 polypeptide is connected to the C-terminals of the heavy chains. In one feature, the mutant IL2 polypeptide is connected to the C-terminals of the heavy chains through a linker sequence comprising SEQ ID NO: 19.

In another embodiment, an alternative molecule of the fusion protein comprises of one or more mutated amino acids to remove proteolytic sites for improving production. In another embodiment, an alternative molecule of the fusion protein comprises one or more mutated amino acids to remove glycosylation sites without otherwise altering the function of the protein for generating a more homogeneous product. In another embodiment, an alternative molecule of the fusion protein comprises of an alternate secretory sequence instead of a natural secretory sequence for improving secretion.

In another aspect, the present invention provides a fusion protein that combines an immune checkpoint antibody (anti-CP antibody) with an IL2 mutant that is less selective towards the high affinity receptor (or interchangeably, an intermediate-affinity receptor selective mutant, MutIL2), the fusion protein is a bispecific design with a first arm corresponding to an anti-CP antibody and a second arm consisting of MutIL2 fused to the Fc portion (FIG. 1B). In addition, the presence of the Fc portion of the protein allows the use of the Fc neonate receptor pathway to enhance the half-life of the fusion protein by orders of magnitude.

In one feature, the anti-CP antibody is an anti-PDL1 antibody. Perfectly, the anti-PDL1 antibody has one or more of the following features that can increase the anti-tumor capability of the fusion protein: (a) it binds PDL1 with a Kd<100 nM to purified protein as well as protein-expressed on cell surface; (b) it blocks PDL1-PD1 interaction in vitro; and (c) it de-represses PDL1-mediated repression of effector T cells in activated PBMC cultures.

In one embodiment, the bispecific antibody is an antibody of any available isotype or any known mutant forms of Fc region that inactivates, reduces or enhances ADCC and/or CDC functions. In a perfect embodiment, the bispecific antibody is an antibody of IgG1 isotype. In some embodiments, the first arm of the bispecific antibody includes a pair of heavy chain variable region and light chain variable region where their respective sequences consist essentially of the following: (a) SEQ ID NO: 3 and SEQ ID NO: 6; (b) SEQ ID NO: 9 and SEQ ID NO: 12; or (c) SEQ ID NO: 15 and SEQ ID NO: 18. In other embodiments, the anti-PDL1 antibody includes a pair of heavy chain and light chain where their respective sequences consist essentially of the following: (a) SEQ ID NO: 2 and SEQ ID NO: 5; (b) SEQ ID NO: 8 and SEQ ID NO: 11; or (c) SEQ ID NO: 14 and SEQ ID NO: 17.

In one feature, the MutIL2 has one or both of the following features that can increase the anti-tumor capability of the fusion protein: (a) reduce ability to activate CTLL2 and human and mouse $T_{reg}$ while retaining its ability to activate effector T cells or NK cells; and (b) up to 10-fold to over 1000-fold increase in its relative ability to activate $T_{eff}/T_{reg}$ compared to wild type IL2. In a further embodiment, the MutIL2 includes amino acid sequence substantially identical to the amino acid sequences selected from the group consisting of SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57 and combinations thereof.

In another embodiment, an alternative molecule of the fusion protein comprises one or more mutated amino acids to remove proteolytic sites for improving production. In another embodiment, an alternative molecule of the fusion protein comprises one or more mutated amino acids to remove glycosylation sites without otherwise altering the function of the protein for generating a more homogeneous product. In another embodiment, an alternative molecule of the fusion protein comprises an alternate secretory sequence instead of a natural secretory sequence for improving secretion.

In another aspect, the present invention also provides a fusion protein that is a polypeptide consisting of an antigen-binding polypeptide and an IL2 mutant that is less selective towards the high affinity receptor (or interchangeably, an intermediate-affinity receptor selective mutant, MutIL2) (FIG. 2). This approach would add a linker sequence between the two portions for instance. The polypeptide is a smaller molecule that could be expressed in tumor-targeting bacteria. In some embodiments, the antigen-binding polypeptide is selected from the group consisting of an anti-CP scFv, a ligand or a portion of the ligand. In some embodiments, the anti-CP scFv is an anti-PDL1 scFv. In some embodiments, the ligand is PD1 or CTLA4. In some embodiments, the antigen-binding polypeptide is selected from the group consisting of immunotherapeutic antibodies, such as anti-GD2, anti-TGFbeta, anti-CD47, anti-OX40, anti-IBB or an immunotherapeutic antibody that can work in concert with MutIL2 of this invention.

In one feature, the MutIL2 has one or both of the following features that can increase the anti-tumor capability of the fusion protein: (a) reduce ability to activate CTLL2 and human and mouse $T_{reg}$ while retaining its ability to activate effector T cells or NK cells; and (b) up to 10-fold to over 1000-fold increase in its relative ability to activate $T_{eff}/T_{reg}$ compared to wild type IL2. In a further embodiment, the MutIL2 includes amino acid sequence substantially identical to the amino acid sequences selected from the group consisting of SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57 and combinations thereof.

In one feature, the linker sequence is a flexible serine-glycine linker or other known variants or linkers. In one embodiment, the linker sequence is SEQ ID NO: 19.

In another embodiment, an alternative molecule of the fusion protein comprises one or more mutated amino acids to remove proteolytic sites for improving production. In another embodiment, an alternative molecule of the fusion protein comprises one or more mutated amino acids to remove glycosylation sites without otherwise altering the function of the protein for generating a more homogeneous product. In another embodiment, an alternative molecule of the fusion protein comprises an alternate secretory sequence instead of a natural secretory sequence for improving secretion.

In another aspect, the present invention provides an engineered protein, comprising a therapeutic protein, e.g., a tumor-targeting agent, that is fused to or otherwise connected to a mutant of the IL2 polypeptide selective for an intermediate-affinity receptor. In some embodiments, the therapeutic protein is a therapeutic antibody, tumor-targeting antibody, a tumor antigen-binding polypeptide, or a tumor-targeting oligonucleotides, e.g. aptamers or small molecules. In some embodiments, the tumor-targeting antibody is an immune checkpoint antibody. In some embodiments, the present invention provides an engineered protein, comprising a therapeutic protein and a mutant Interleukin-2 (IL2) polypeptide. In some embodiments, therapeutic protein is a therapeutic antibody or a tumor antigen-binding polypeptide. In some embodiments, the tumor-targeting antibody or the therapeutic antibody is an anti-PD-L1 antibody, an anti-CD19 antibody, an anti-MUC1 antibody, an anti-CD22 antibody, an anti-HER2 antibody, an anti-CD20 antibody, an anti-CD80 antibody, an anti-BCMA antibody, an anti-EGFR antibody, or an anti-Mesothelin antibody. The tumor-targeting agents can help deliver IL2 into the tumor and reduce systemic side effects. And the mutant IL2 can directly activate effector cells to enhance the anti-tumor activity of the tumor-targeting agents.

In one feature, the MutIL2 has one or both of the following features that can increase the anti-tumor capability of the fusion protein: (a) reduce ability to activate CTLL2 and human and mouse $T_{reg}$ while retaining its ability to activate effector T-cells or NK cells; and (b) up to 10-fold to over 1000-fold increase in its relative ability to activate $T_{eff}/T_{reg}$ compared to wild type IL2. In a further embodiment, the MutIL2 includes amino acid sequences substantially identical to the amino acid sequences selected from the group consisting of SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57 and combinations thereof.

In another aspect, the present invention provides a pharmaceutical composition that includes a fusion protein of any aspect above. The pharmaceutical composition further includes a pharmaceutically acceptable excipient, carrier, or diluent.

In a related aspect, the present invention provides a method of treating a subject in need thereof for a pathological condition therapeutically, said method comprising administering to said subject a therapeutically effective amount of the fusion protein disclosed herein. The method may further include a step of administering a second and different therapeutic antibody against at least one cell-surface antigen indicative of said condition. The condition being treated may be a mammalian cancer, an infection, and so on.

Preferably, the spectrum of mammalian cancers to be treated is selected from the a group consisting of ovarian cancer, colon cancer, breast cancer, lung cancer, myelomas, neuroblastic-derived CNS tumors, monocytic leukemias, B-cell derived leukemias, T-cell derived leukemias, B-cell derived lymphomas, T-cell derived lymphomas, mast cell derived tumors, melanoma, bladder cancer, gastric cancer, liver cancer, urothelial carcinoma, cutaneum carcinoma, renal cancer, head and neck cancer, pancreatic cancer, and combinations thereof. In some embodiments, the spectrum of mammalian cancers to be treated is selected from the a group consisting of melanoma, lung cancer, renal cancer, head neck cancer, gastric cancer, lymphoma, ovarian cancer, colon cancer, breast cancer, lung cancer, myelomas, brain tumors, leukemias, lymphomas, bladder cancer, liver cancer, urothelial carcinoma, cutaneous carcinoma, pancreatic cancer, and combinations thereof.

In yet another aspect, the invention provides a method of treating a subject in need thereof for similar conditions prophylactically, said method comprising administering to said subject a prophylactically effective amount of the pharmaceutical composition of the invention. The method may further include a step of administering a vaccine against said condition. In one embodiment, the condition is a cancer.

In a further aspect, the invention provides a mammalian expression system that produces the fusion protein described above.

DETAILED DESCRIPTION OF INVENTION

Figure 1A:
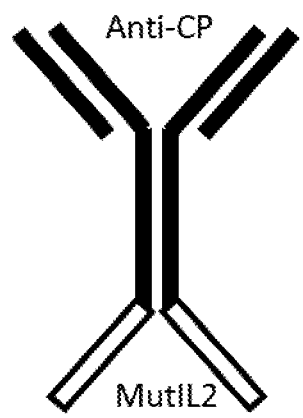
FIGS. 1A and 1B schematically depicts fusion protein design of the present invention.
Figure 1B:
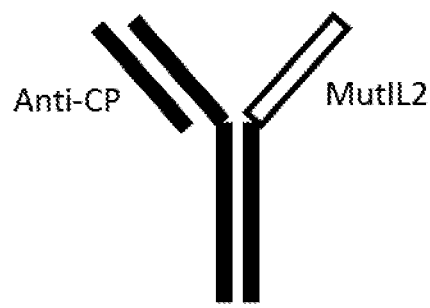
Figure 2:
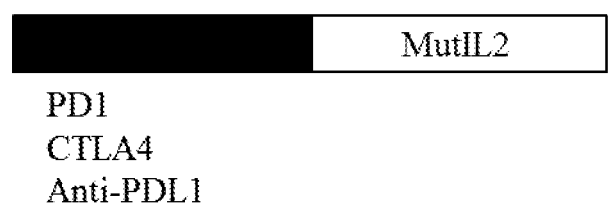
FIG. 2 schematically depicts alternate fusion protein design of the present invention.

Unless otherwise noted, technical terms are used according to conventional usage.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure. Unless indicated otherwise, "about" is +/−10% of the recited value(s).

An "antigen-binding polypeptide" is a polypeptide comprising a portion that binds to an antigen. Examples of antigen-binding polypeptides include antibodies, antibody fragments (e.g., an antigen binding portion of an antibody), antibody derivatives, and antibody analogs.

The term "consist essentially of" or "substantially identical" as used herein, refers to at least 60%, or 80%, or, more preferably, 85%, 90%, 95%, or even 100%, identity, for example, to a selected amino acid sequence.

An antigen binding polypeptide or protein can have, for example, the structure of a naturally occurring antibody (also known as "immunoglobulin"). Each naturally occurring antibody is composed of two identical pairs of polypeptide chains, each pair having one "light" (about 25 kDa) and one "heavy" chain (about 50-70 kDa). The variable regions of each light/heavy chain pair form the antibody-binding site such that an intact antibody has two binding sites.

The variable regions of naturally occurring antibody chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5$^{th}$ Ed., US Dept. of Health and Human Services, PHS, NIH, NIH Publication no. 91-3242, 1991. Other numbering systems for the amino acids in immunoglobulin chains include IMGT (international ImMunoGeneTics information system; Lefranc et al., Dev. Comp. Immunol. 29:185-203; 2005) and AHo (Honegger and Pluckthun, J. Mol. Biol. 309(3):657-670; 2001). Within the variable regions, the CDR 1, CDR 2 and CDR 3 regions are important, with CDR3 region being the most important. These can be identified by standard bioinformatics and mutagenesis experiments.

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecific antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

The term "antibody" or "Ab" (and their plural forms), as used herein, broadly refers to any immunoglobulin (Ig) molecule comprised of four polypeptide chains, two heavy (H) chains and two light (L) chains, or any functional fragment, mutant, variant, derivative or analog thereof, which retains the essential and specific epitope-binding features of an Ig molecule. Such fragment, mutant, variant, derivative or analog antibody formats are known in the art, and include, inter alia, Fab, F(ab'), F(ab')$_2$, Fv, single-chain antibodies (scFv), single-domain antibodies (sdAbs), complementarity determining region (CDR) fragments, chimeric antibodies, diabodies, triabodies, tetrabodies, and polypeptides that contain at least a portion of an immunoglobulin that is sufficient to confer specific antigen binding to the polypeptide. Antibody fragments, derivatives and analogs may be produced by recombinant DNA techniques or by enzymatic or chemical cleavage of intact antibodies.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634; 6,696,245, US App. Pub. 20/0202512; 2004/0202995; 2004/0038291; 2004/0009507; 2003/0039958, and Ward et al., *Nature* 341: 544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, *Science* 242:423-26 and Huston et al., 1988, *Proc. Natl. Acad. Sci. USA* 85:5879-83). Diabodies are bivalent antibodies comprising two polypeptide chains, where each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen-binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra; Lefranc et al., supra and/or Honegger and Pluckthun, supra. One or more CDRs may be incorporated into a molecule either covalently or noncovalently to make it an antigen binding protein. An antigen binding polypeptide may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

A fusion protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" or "humanized antibody" includes all antibodies that have one or more variable and constant regions derived from human immunoglobulin sequences. In one embodiment, all of the variable and constant domains are derived from human immunoglobulin sequences (a fully human or humanized antibody). These antibodies may be prepared in a variety of ways, including through the immunization with an antigen of interest of a mouse that is genetically modified to express antibodies derived from human heavy and/or light chain-encoding genes. A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

Activated T cells express PD1 on their cell surface. Binding of PD-L1 to PD1 activates PD1 and suppresses the PD 1$^+$ T cells. A "neutralizing antibody" or an "inhibitory antibody" is an antibody that blocks the activation of PD1 when an excess of the anti-PD-L1 antibody reduces the amount of said activation by at least about 20% using an assay such as those described herein in the Examples. In various embodiments, the antigen binding protein reduces the amount of activation of PD1 by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, Bowie et al., 1991, *Science* 253:164.

A fusion protein "specifically binds" to an antigen (e.g., human PD-L1) if it binds to the antigen with a dissociation constant of 100 nanomolar or less.

An "antigen binding domain", "antigen binding region," or "antigen binding site" is a portion of an antigen binding protein that contains amino acid residues (or other moieties) that interact with an antigen and contribute to the antigen binding protein's specificity and affinity for the antigen. For an antibody to specifically bind to its antigen, it will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein.

As used herein, the terms "polynucleotide", "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding a fusion protein, an antibody, or a fragment, derivative, mutant, or variant thereof.

A "vector" is a nucleic acid that can be used to introduce another nucleic acid linked to it into a cell. One type of vector is a "plasmid", which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego, Calif. and Baron et al., 1995, *Nucleic Acids Res.* 23:3605-06.

Terms such as "therapeutic" as used herein refer to the quality and ability to cure, slow down, lessen symptoms of, and/or halt progression of a diagnosed pathologic condition or disorder. Thus a therapeutic protein or polypeptide is one that has the above quality and ability. A subject is successfully "treated" according to the methods of the present invention, for example, if the patient shows one or more of the following: a reduction in the number of or complete absence of cancer cells; a reduction in the tumor size; inhibition of or an absence of cancer cell infiltration into peripheral organs including the spread of cancer into soft tissue and bone; inhibition of or an absence of tumor metastasis; inhibition or an absence of tumor growth; relief of one or more symptoms associated with the specific cancer; reduced morbidity and mortality; and improvement in quality of life.

Preferably, the broad spectrum of mammalian cancers to be treated by compositions of the present invention is selected from the group consisting of ovarian cancer, colon cancer, breast cancer, lung cancer, myelomas, neuroblastic-derived CNS tumors, monocytic leukemias, B-cell derived leukemias, T-cell derived leukemias, B-cell derived lymphomas, T-cell derived lymphomas, mast cell derived tumors, melanoma, bladder cancer, gastric cancer, liver cancer, urothelial carcinoma, cutaneum carcinoma, renal cancer, head and neck cancer, pancreatic cancer, and combinations thereof. More broadly, any cancer where at least a fraction of the tumor cells express detectable amount of PD-L1 can potentially be treated by the composition of the invention.

Fusion proteins or polypeptides of the present disclosure can be produced using any standard methods known in the art. In one example, the polypeptides are produced by recombinant DNA methods by inserting a nucleic acid sequence (e.g., a cDNA) encoding the polypeptide into a recombinant expression vector and expressing the DNA sequence under conditions promoting expression.

Nucleic acids encoding any of the various fusion proteins or polypeptides disclosed herein may be synthesized chemically. Codon usage may be selected so as to improve expression in a cell. Such codon usage will depend on the cell type selected. Specialized codon usage patterns have been developed for E. coli and other bacteria, as well as mammalian cells, plant cells, yeast cells and insect cells. See for example: Mayfield et al., *Proc. Natl. Acad. Sci. USA.* 2003 100(2):438-42; Sinclair et al. *Protein Expr. Purif.* 2002 (1):96-105; Connell N D. *Curr. Opin. Biotechnol.* 2001 12(5):446-9; Makrides et al. *Microbiol. Rev.* 1996 60(3): 512-38; and Sharp et al. *Yeast.* 1991 7(7):657-78.

General techniques for nucleic acid manipulation are described for example in Sambrook et al., *Molecular Cloning: A Laboratory Manual, Vols.* 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

The bispecific molecule disclosed herein can also be produced using cell-translation systems. For the sake of manufacturing ease, there are several ways to ensure that the heterodimeric bispecific molecule is preferentially produced in the cells by using complementary mutations on the two heavy molecules.

The fusion protein or polypeptide of the present disclosure can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

Another version of the molecule of the fusion protein has mutations in one or more amino acids to remove proteolytic sites to improve production.

Another version of the molecule of the fusion protein has mutations in one or more amino acids to remove glycosylation sites without otherwise altering the function of the protein to generate a more homogeneous product.

Another version of the molecule of the fusion protein uses an alternate secretory sequence instead of the natural antibody secretory sequence to improve secretion.

The fusion proteins or polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combination of these. After purification, polypeptides may be exchanged into different buffers and/or concentrated by any of a variety of methods known to the art, including, but not limited to, filtration and dialysis.

The purified fusion protein or polypeptide is preferably at least 85% pure, more preferably at least 95% pure, and most preferably at least 98% pure. Regardless of the exact numerical value of the purity, the polypeptide is sufficiently pure for use as a pharmaceutical product.

Post-Translational Modifications of Polypeptides

In certain embodiments, the fusion protein or polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. Biochemistry. 2001 31; 40(30):8868-76. Effects of such non-amino acid elements on the functionality of a polypeptide may be tested for its antagonizing role in PD-L1 or PD-1 function, e.g., its inhibitory effect on angiogenesis or on tumor growth.

In one embodiment, biological activity refers to its ability to bind to PD-L1, as assessed by KD, kon or koff rates. In one specific embodiment, the pegylated polypeptide protein shows an increase in binding to human PD-L1 relative to the unpegylated counterpart. In another embodiment, the biological activity refers to blockage of PD-L1/PD1 interaction.

Therapeutics, Vaccines & Administration

The present disclosure further features methods for treating conditions or preventing pre-conditions. Preferred examples are conditions that are characterized by cellular hyperproliferation and sustained infection. Techniques and dosages for administration vary depending on the type of specific polypeptide and the specific condition being treated. Because regulatory agencies require that a protein reagent to be used as a therapeutic be formulated with acceptably low levels of pyrogens, therapeutic formulations of the present invention can be distinguished from other formulations for being substantially pyrogen free, or at least contain no more than acceptable levels of pyrogen as determined by the appropriate regulatory agency (e.g., FDA).

Pharmaceutical formulations of the present invention may include at least one pharmaceutically acceptable diluent, carrier, or excipient. Excipients included in the formulations will have different purposes depending, for example, on the kind of gene construct or effector cells used, and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents.

In another embodiment of the invention, a pharmaceutical formulation of the invention is administered into the patient. Exemplary administration modes include, but are not limited to, intravenous injection. Other modes include, without limitation, intratumoral, intradermal, subcutaneous (s.c., s.q., sub-Q, Hypo), intramuscular (i.m.), intraperitoneal (i.p.), intra-arterial, intramedullary, intracardiac, intra-articular (joint), intrasynovial (joint fluid area), intracranial, intraspinal, and intrathecal (spinal fluids). Any known device useful for parenteral injection or infusion of the formulations can be used to effect such administration. As used herein, the terms "treat", "treating", and "treatment" have their ordinary and customary meanings, and include one or more of: blocking, ameliorating, or decreasing in severity and/or frequency a symptom of a disease (e.g., cancer) in a subject, and/or inhibiting the growth, division, spread, or proliferation of cancer cells, or progression of cancer (e.g., emergence of new tumors) in a subject. Treatment means blocking, ameliorating, decreasing, or inhibiting by about 5% to about 100% versus a subject in which the methods of the present invention have not been practiced. Preferably, the blocking, ameliorating, decreasing, or inhibiting is about 100%, 99%, 95%, 90%, 80%, 70%, 60%, 50%, 40%, 30%, 20%, 10%, or 5% versus a subject in which the methods of the present invention have not been practiced.

The invention also provides a kit comprising one or more containers filled with quantities of gene constructs encoding the fusion protein or polypeptides of the invention, with pharmaceutically acceptable excipients. The kit may also include instructions for use. Associated with the kit may further be a notice in the form prescribed by a governmental agency regulating the manufacture, use or sale of pharmaceuticals or biological products, which notice reflects approval by the agency of manufacture, use or sale for human administration.

EXAMPLES

Example 1

Anti-PDL1 light chain (IgL) and anti-PD-L1 heavy chain (IgH) fused to MutIL2 were cloned into a single eukaryotic expression vector with two expression cassettes—pCHO 1.0 vector. Other similar vectors are commercially available. Moreover, the two genes could be cloned in separate vectors. The vector was transfected into Expi293 cells following the manufacturer's recommendations. The protein was secreted into the supernatant and purified to >95% purity using a HiTrap Protein A column using standard procedures. The purified proteins were compared with wild type IL2 for their ability to preferentially activate $T_{\mathit{eff}}$ cells than $T_{\mathit{reg}}$ cells. In this application, fusions are named using both anti-PDL1 antibody and the specific MutIL2. For instance, E1M1 contains the E1 antibody and a MutIL2 IL2M1.

Example 2

Figure 3A:
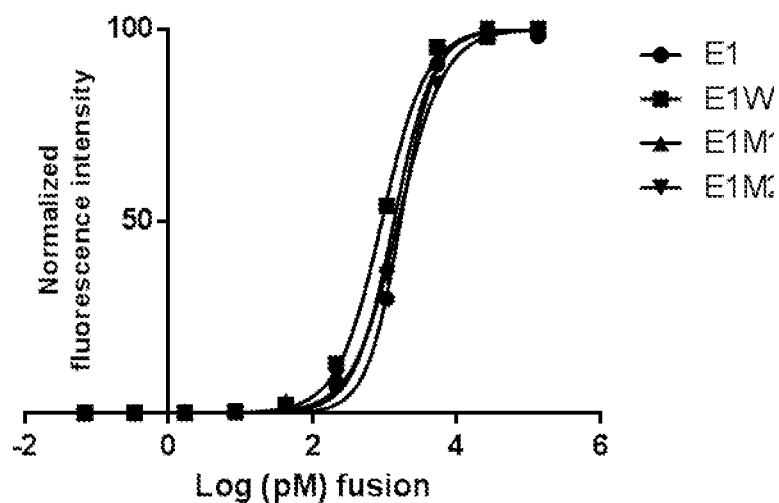
FIGS. 3A and 3B show representative data comparing binding of cell surface PDLL by parental antibodies versus wild type and mutant IL2 fusion proteins of the present invention.
Figure 3B:
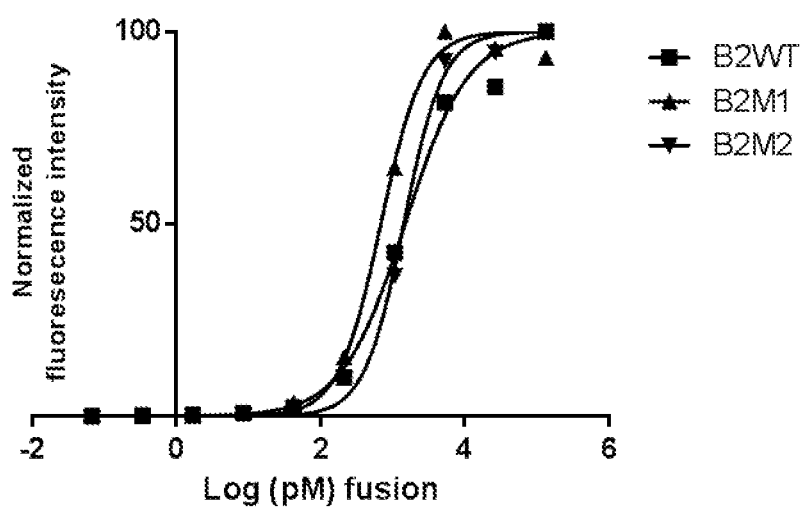

To test the ability of the proteins to bind cell surface PDL1, we used DLD1 cells expressing transgenically expressed human PDLL. Similar results could be obtained either with transgenic expression in other cell lines or by using cells that naturally express PDL1 or are induced to express PDL1 by interferon γ treatment. Briefly, $10^5$ cells were incubated with different concentrations of the protein for 30 minutes at 4° C. Cells were washed with PBS and incubated with a fluorescent, anti-human-IgG antibody for 30 minutes at 4° C. Cells were again washed with PBS and binding was detected by FACS. FIG. 3 shows that the fusions with different IL2 mutations do not affect their PDL1 binding (Table 2).

TABLE 2

EC50 for cell surface PDL1 binding by IL2 fusions

|  | Mean (pM) | SD |
| --- | --- | --- |
| E1 | 1958 | 297 |
| E1WT | 2006 | 1236 |
| E1M1 | 2444 | 782 |
| E1M2 | 3204 | 1294 |
| B2WT | 1482 | — |
| B2M1 | 688 | — |
| B2M2 | 1427 | — |

Similarly, to test the ability of the antibody part to block PD1-PDL1 interactions, receptor blocking assays were performed in two distinct ELISA formats—with either biotinylated Fc-PDL1 binding to PD1-coated plates or biotinylated Fc-PD1 binding to PDL1-coated plates. In both cases, binding was detected by using streptavidin linked horse radish peroxidase. Table 3 shows that the exemplary PDL1 antibodies show high potency in blocking PD1-PDL1 interaction.

TABLE 3

IC50 for blocking PD1-PDL1 binding by anti-PDL1 antibodies

|  | PD1 coated | PDL1 coated |
| --- | --- | --- |
| E1 | 1.26 nM | 1.53 nM |
| B2 | 1.39 nM | 0.80 nM |
| E3 | 92.74 nM | 16.57 nM |

Example 3

Figure 4:
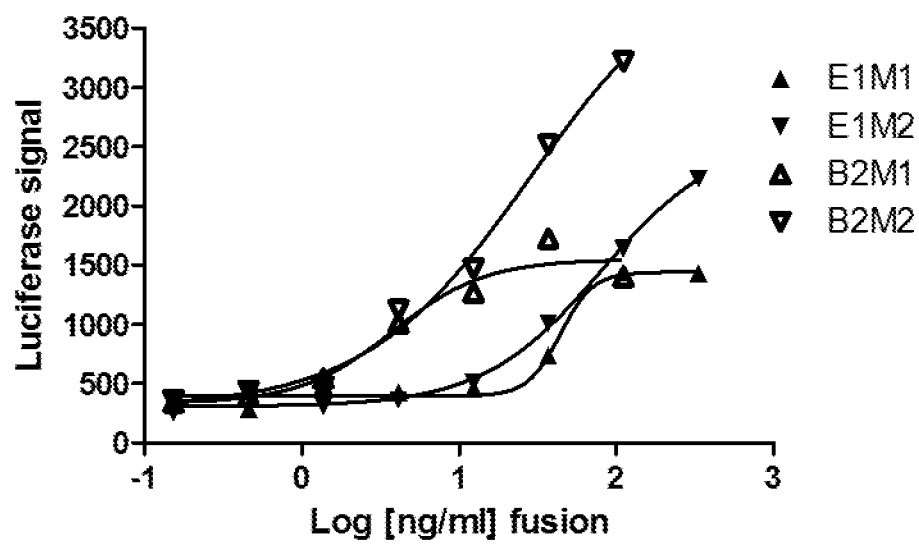
FIG. 4 shows representative ADCC activity of various fusion proteins.

To test ADCC activity, we used a commercial ADCC assay kit (Promega) that relies on Jurkat cells with an Fc receptor-responsive luciferase gene. Co-incubation of these cells with PDL1+ MDA-MB-231 cells and an ADCC+ antibody triggers Fc receptor engagement which can be measured as luciferase activity. FIG. 4 shows that various fusion proteins of the invention show ADCC activity.

Example 4

Figure 5:
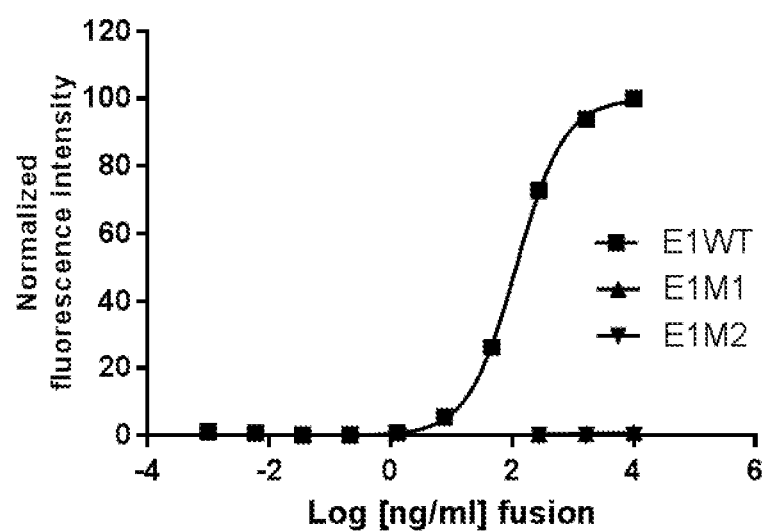
FIG. 5 shows representative data comparing binding of cell surface trimeric (high-affinity) IL2 receptor by wild type IL2 fusion protein versus two mutant forms of IL2 fusion protein of the present invention.

To test the ability of the mutant proteins to bind IL2 receptors on CTLL2 cells, $10^5$ cells were incubated with different concentrations of the protein for 30 minutes at 4C. Cells were washed with PBS and incubated with a fluorescent, anti-human-IgG antibody for 30 minutes at 4° C. Cells were again washed with PBS and binding was detected by FACS. FIG. 5 shows that fusions with different IL2 mutants show dramatic reduction in binding to the high affinity IL2 receptor on CTLL2 cells compared to the fusion with wildtype IL2.

Example 5

Figure 6:
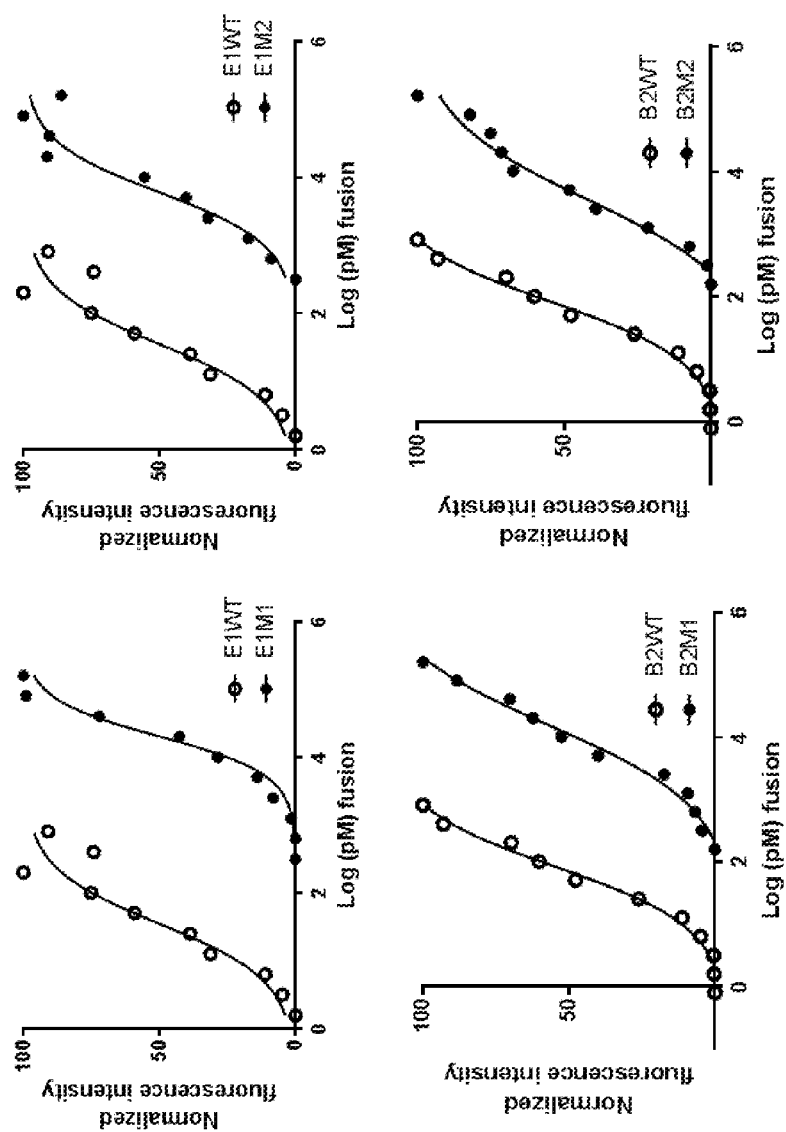
FIG. 6 shows representative data comparing the ability of wild type IL2 fusion proteins versus various mutant forms of IL2 fusion protein of the present invention to trigger and support proliferation of CTLL2 cells (surrogate for $T_{reg}$ cells) as measured by AlamarBlue assay.

To test the ability of the mutant proteins to activate CTLL2 cells (surrogate for $T_{\mathit{reg}}$ cells), $10^4$ cells were cultured in the presence of different concentrations of mutant or wild type IL2 fusion protein for 44 hours. Relative viable cell counts were determined by incubating the cultures with AlamarBlue for 1-4 hours and measuring fluorescence intensity using a fluorescent plate reader. FIG. 6 shows that fusions with different IL2 mutants show a greater than 100-fold reduced ability to support proliferation of CTLL2 cells compared to the fusion with wild type IL2 (Table 4). This is true with fusions containing either PDL1 antibody. The wild type fusion is comparable to recombinant IL2.

TABLE 4

EC50 for CTLL2 proliferation by IL2 fusions

|  | Mean (pM) | SD |
| --- | --- | --- |
| E1WT | 29 | 6 |
| E1M1 | 19520 | 707 |
| E1M2 | 9753 | 3779 |
| B2WT | 88 | 6 |
| B2M1 | 9901 | 5156 |
| B2M2 | 3312 | 189 |

Example 6

Figure 7:
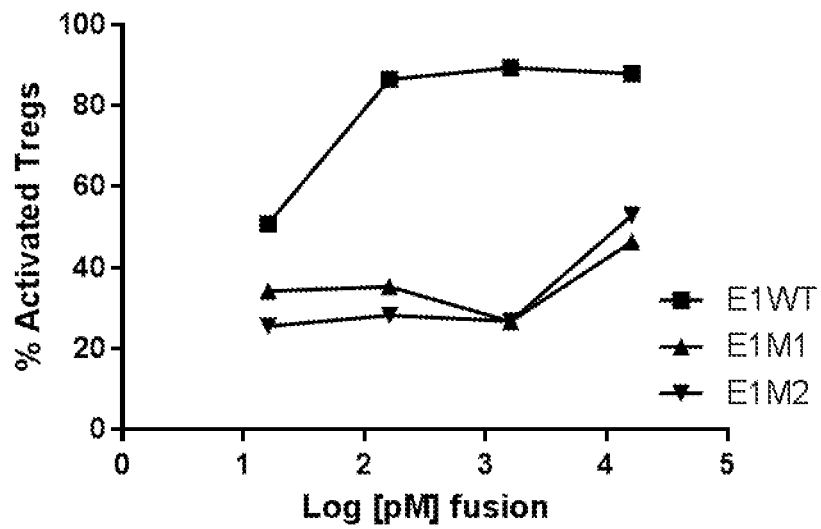
FIG. 7 shows representative data comparing the ability of wild type IL2 fusion proteins versus various mutant forms of IL2 fusion protein of the present invention to support mouse $T_{reg}$ cells survival and activation.
Figure 8:
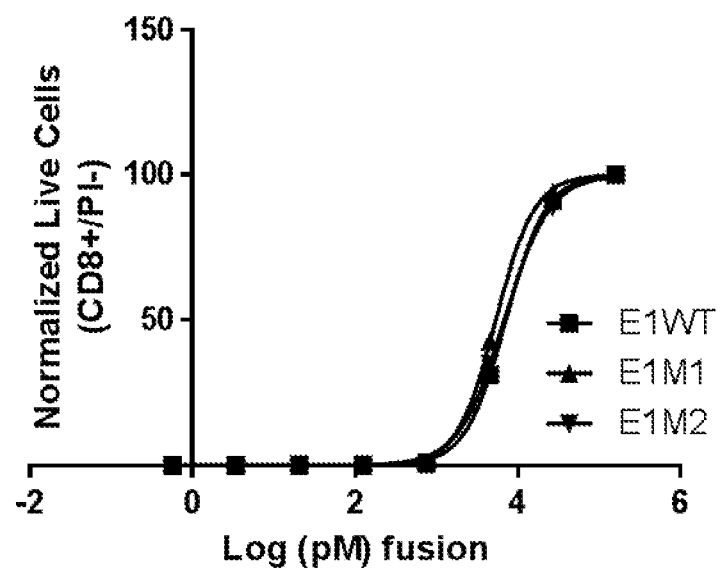
FIG. 8 shows representative data comparing the ability of wild type IL2 fusion proteins versus various mutant forms of IL2 fusion protein of the present invention to support mouse CD8+ T cells (example of $T_{eff}$ cell) survival and proliferation.

To test the ability of the mutant proteins to activate various mouse T-cell subsets, we used cells from a variety of sources. Mouse spleens or lymph nodes were used to isolate CD4, CD8 or regulatory T cells using Stem Cell Technologies magnetic bead-based cell isolation kit following the manufacturer's recommendations. Mouse NK cells assays were done with total splenocytes. Other isolation procedures are commercially available. Human T cell subsets and NK cells were commercially purchased but can be isolated from PBMCs using kits similar to those for mouse cells. Different cell types were incubated with varied amounts of mutant or wild type IL2 fusion protein. For instance, $2.5 \times 10^4$-$10^5$ mouse T cells were used for mouse T-cell experiments. For mouse NK cells, $1$-$5 \times 10^6$ splenocytes were used. For $T_{\mathit{reg}}$ cultures, cells were activated with plate bound anti-CD3 antibodies and incubated as well with a mouse IL2 neutralizing antibody. After 4 days of growth, cells proliferation was measured by direct counting (with or without propidium iodide based exclusion of dead cells) or by CFSE dilution using FACS. In addition, expression of activation markers was also assessed e.g. CD44 for mouse CD8 cells. FIG. 7 shows that fusions with different IL2 mutants show a significant reduction in their ability to activate and support the survival of $T_{reg}$ cells when compared to the fusion with wild type IL2. FIG. 8 and Table 5 show that IL2 mutant fusions are comparable to the wildtype IL2 fusion protein in their ability to support proliferation of mouse CD8+ T-cells. The wild type IL2 fusion is comparable to recombinant IL2 in both assays.

FIG. 6, FIG. 7 and FIG. 8 indicate that fusions with different IL2 mutants show a greater than 100-fold increase in their relative ability to activate $T_{eff}/T_{reg}$ compared to wild type IL2 fusion.

TABLE 5

EC50 for mouse CD8 T cell survival and proliferation by IL2 fusions

|  | Mean (pM) | SD |
|---|---|---|
| E1WT | 8095 | 1052 |
| E1M1 | 7654 | 2348 |
| E1M2 | 7947 | 1197 |
| B2WT | 5921 | 1461 |
| B2M1 | 4875 | 1604 |
| B2M2 | 7651 | 1969 |

Example 7

Figure 9:
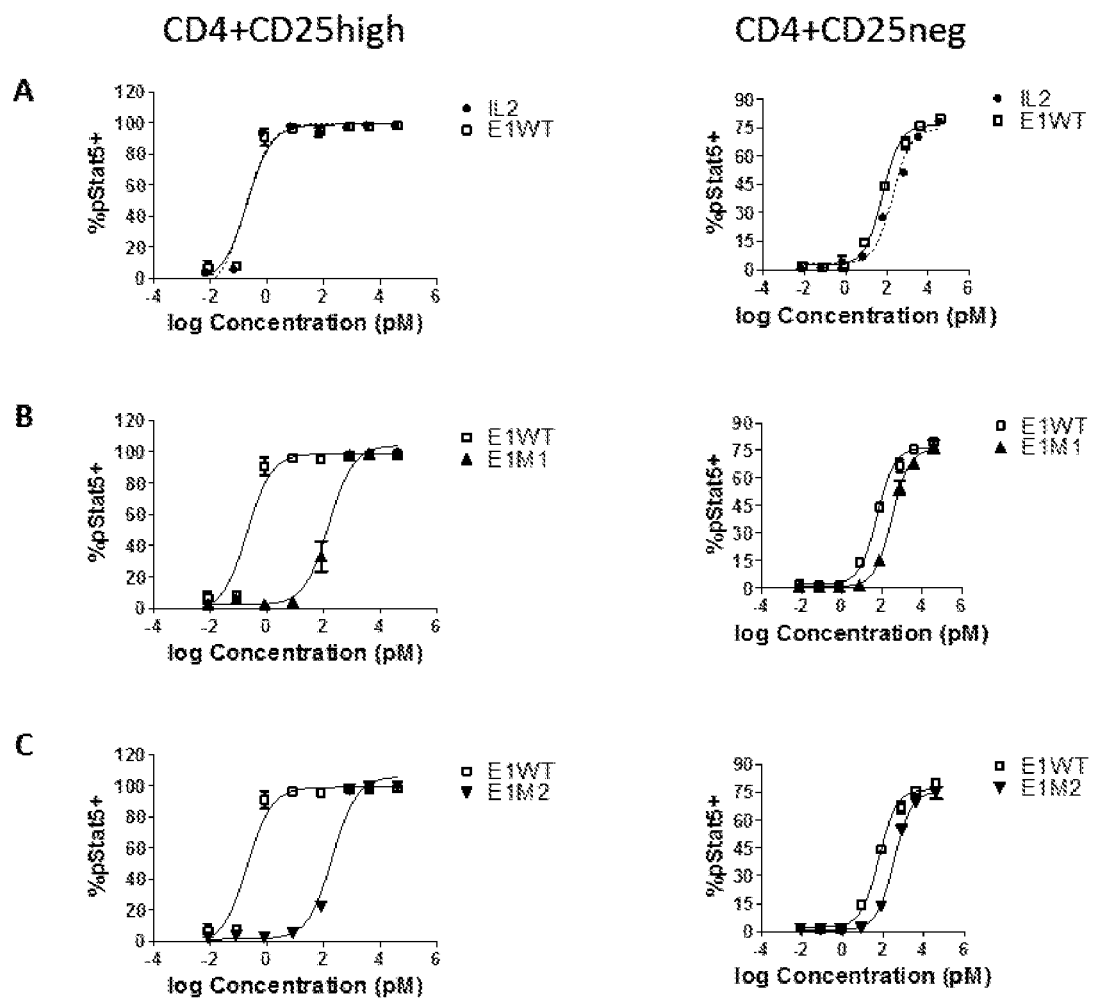
FIGS. 9 and 10 shows representative data comparing the ability of recombinant IL2 and wild type IL2 fusion proteins versus various mutant forms of IL2 fusion protein of the present invention to induce phosphorylation of StatS in $T_{reg}$ and non-$T_{reg}$ CDC cells.
Figure 10:
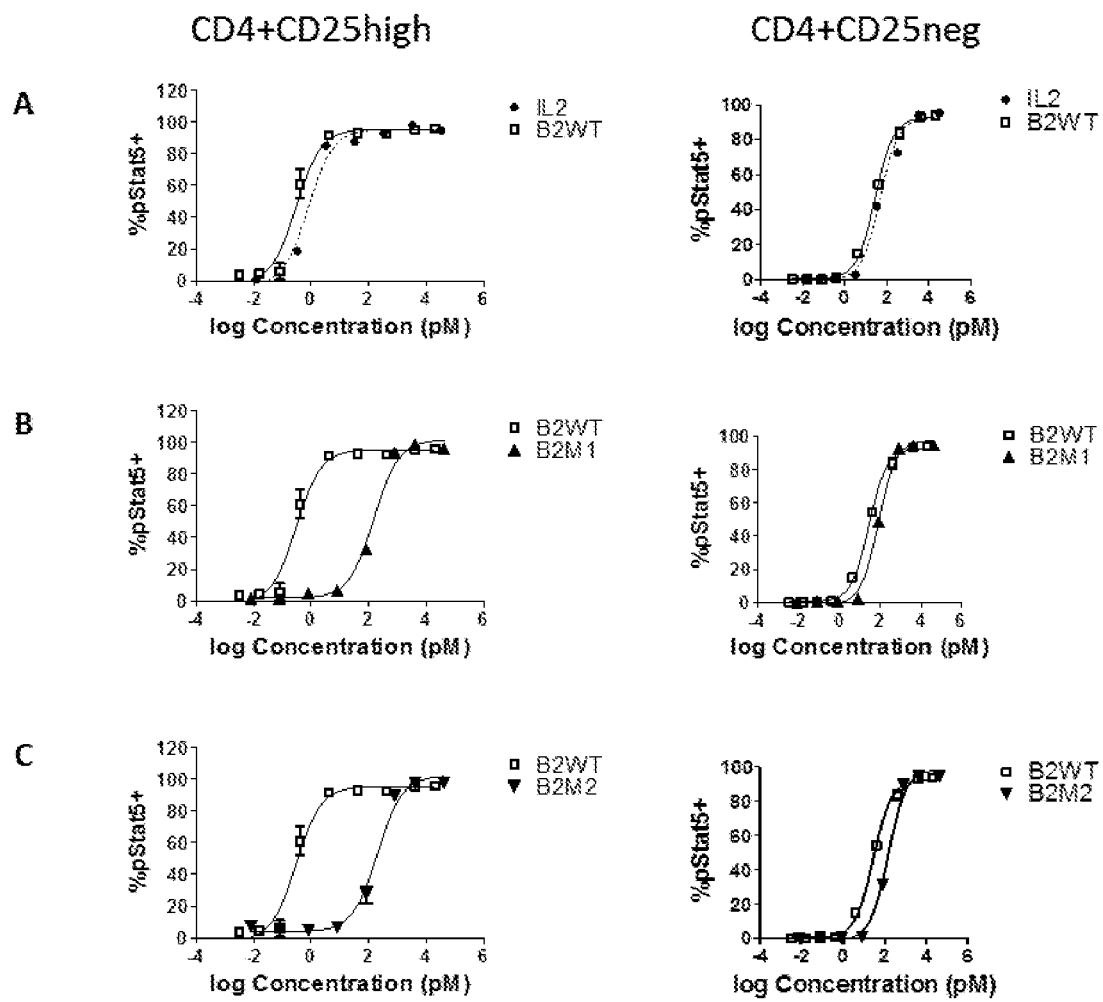
Figure 11:
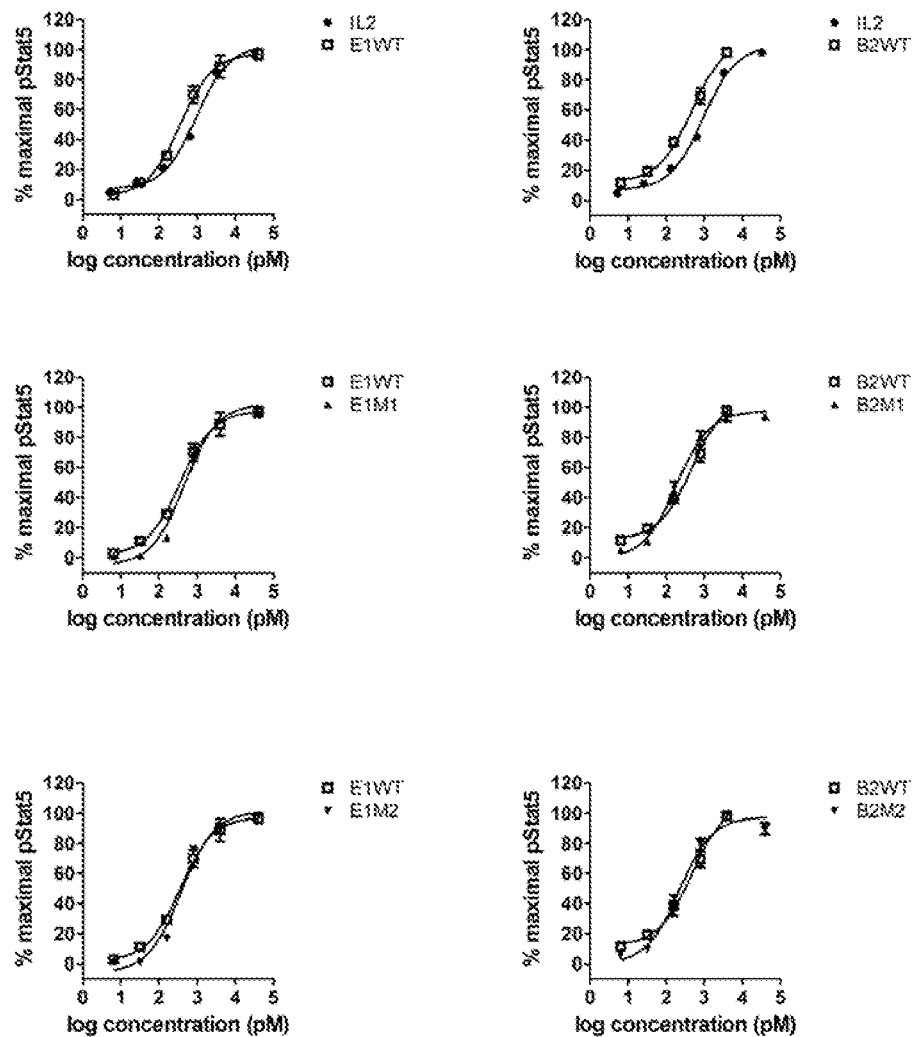
FIG. 11 shows representative data comparing the ability of recombinant IL2 and wild type IL2 fusion proteins versus various mutant forms of IL2 fusion protein of the present invention to induce phosphorylation of StatS in CD8+ effector T cells.

To test the ability of the mutant proteins to activate various human T-cell subsets, we used cells from peripheral blood from healthy human donors. PBMCs were prepared by standard procedures and incubated with recombinant IL2 or different IL2 fusions for 15 minutes. Phosphorylation of Stat5 triggered by engagement of the IL2 receptor on different T-cell subpopulations was assessed by staining for appropriate cell markers and analyzing by FACS. FIG. 9 and FIG. 10 show that compared to the fusion with wild type IL2, the fusions with different IL2 mutants show a significant (about 100-fold) increase in their relative ability to activate non-$T_{reg}/T_{reg}$ (data also summarized in Tables 6-8). FIG. 11 shows that IL2 mutant fusions are comparable to the wildtype IL2 fusion protein in their ability to induce phosphorylation of Stat5 in CD8+ T-cells (data also summarized in Table 9). Compared to the fusion with wild type IL2, the fusions with different IL2 mutants show a significant (about 1000-fold) increase in their relative ability to activate CD8+ T-cells/$T_{reg}$ CD4+ (see Table 10). The wild type IL2 fusion is comparable to recombinant IL2 in each assay. These data shows that the fusions with different IL2 mutants have reduced ability to activate human $T_{reg}$ while retaining its ability to activate effector T-cells, and show a greater than 100-fold increase in its relative ability to activate $T_{eff}/T_{reg}$ compared to the fusion with wild type IL2.

TABLE 6

EC50 for Stat5 phosphorylation by IL2 fusions in $T_{reg}$ (CD4$^+$CD25$^{high}$) cells

|  | Median (pM) | Range (pM) |
|---|---|---|
| IL2 | 0.46 | 0.16-0.9 |
| E1WT | 0.36 | 0.2-0.39 |

TABLE 6-continued

EC50 for Stat5 phosphorylation by IL2 fusions in $T_{reg}$ (CD4$^+$CD25$^{high}$) cells

|  | Median (pM) | Range (pM) |
|---|---|---|
| E1M1 | 148.9 | 108-184 |
| E1M2 | 198.5 | 128-202 |
| B2WT | 0.25 | 0.07-0.3 |
| B2M1 | 91.2 | 53-148 |
| B2M2 | 146.0 | 89-198 |

TABLE 7

EC50 for Stat5 phosphorylation by IL2 fusions in non-$T_{reg}$ (CD4$^+$CD25$^-$) cells

|  | Median (pM) | Range (pM) |
|---|---|---|
| IL2 | 47.0 | 33-217 |
| E1WT | 34.9 | 23-61 |
| E1M1 | 198.1 | 152-336 |
| E1M2 | 207.3 | 188-340 |
| B2WT | 27.7 | 14-36 |
| B2M1 | 83.8 | 80-94 |
| B2M2 | 141.0 | 119-145 |

TABLE 8

EC50 ratios between non-$T_{reg}$ and $T_{reg}$ CD4$^+$ for various IL2 fusions

|  | Ratio |
|---|---|
| IL2 | 102 |
| E1WT | 96 |
| E1M1 | 1.3 |
| E1M2 | 1.0 |
| B2WT | 111 |
| B2M1 | 0.9 |
| B2M2 | 1.0 |

TABLE 9

EC50 for Stat5 phosphorylation by IL2 fusions in CD8$^+$ cells

|  | Mean (pM) | SD |
|---|---|---|
| IL2 | 1236 | 536 |
| E1WT | 258 | 92 |
| E1M1 | 522 | 66 |
| E1M2 | 520 | 199 |
| B2WT | 303 | 234 |
| B2M1 | 342 | 221 |
| B2M2 | 370 | 212 |

TABLE 10

EC50 ratios between CD8$^+$ cells and Treg CD4$^+$ for various IL2 fusions

|  | Ratio |
|---|---|
| IL2 | 2686 |
| E1WT | 714 |
| E1M1 | 4 |
| E1M2 | 3 |
| B2WT | 1216 |
| B2M1 | 4 |
| B2M2 | 3 |

Example 8

For PK studies, female homozygous Tg32 mice (6-8 week-old), were injected with test fusion protein intravenously via tail vein at a dose of 0.1-10 mg/kg into 5 animals per group. Blood was drawn at multiple time points and serum was prepared by centrifugation. Amount of fusion protein was estimated by sandwich ELISA. The titer was normalized to Day 1 after injection.

Figure 12:
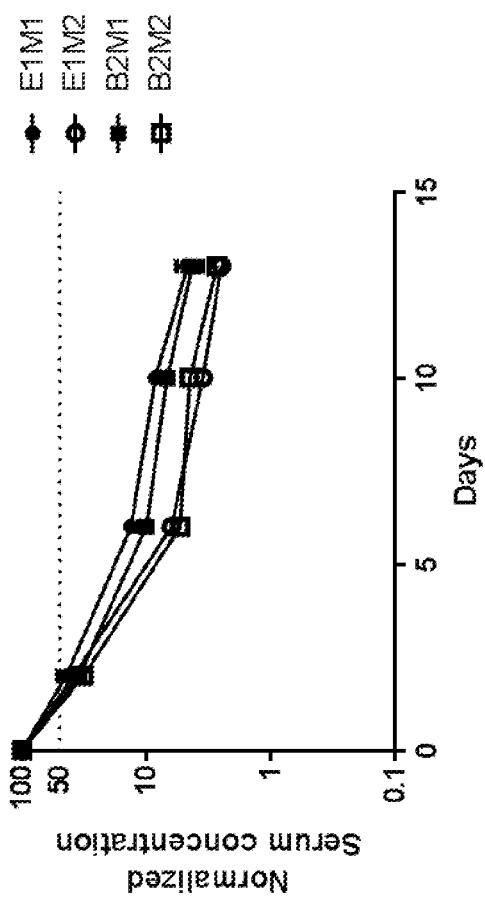
FIG. 12 shows the pharmacokinetic profile of various mutant forms of IL2 fusion protein of the present invention.

FIG. 12 shows the pharmacokinetics of four MutIL2 fusions. The half-lives of the fusions are shown in Table 11. This is significantly longer than the reported half-life of recombinant IL2 by a couple of hours.

TABLE 11

Serum half-life of various MutIL2 fusions

| | E1M1 | E1M2 | B2M1 | B2M2 |
|---|---|---|---|---|
| Half Life(Days) | 1.563 | 1.383 | 1.196 | 1.139 |

Example 9

For mouse pharmacodynamics and toxicology studies, wild type B6 mice were injected with test antibody intravenously via tail vein at a dose of 0.1-10 mg/kg and observed for several days for immune activation and adverse reaction. Blood was drawn on multiple days to assess T-cell and NK cell compartments for expansion. At the end of observation, mice were sacrificed and spleens were analyzed similarly and lungs and livers were assessed for lymphocyte infiltration and other immune reactions.

Figure 13:
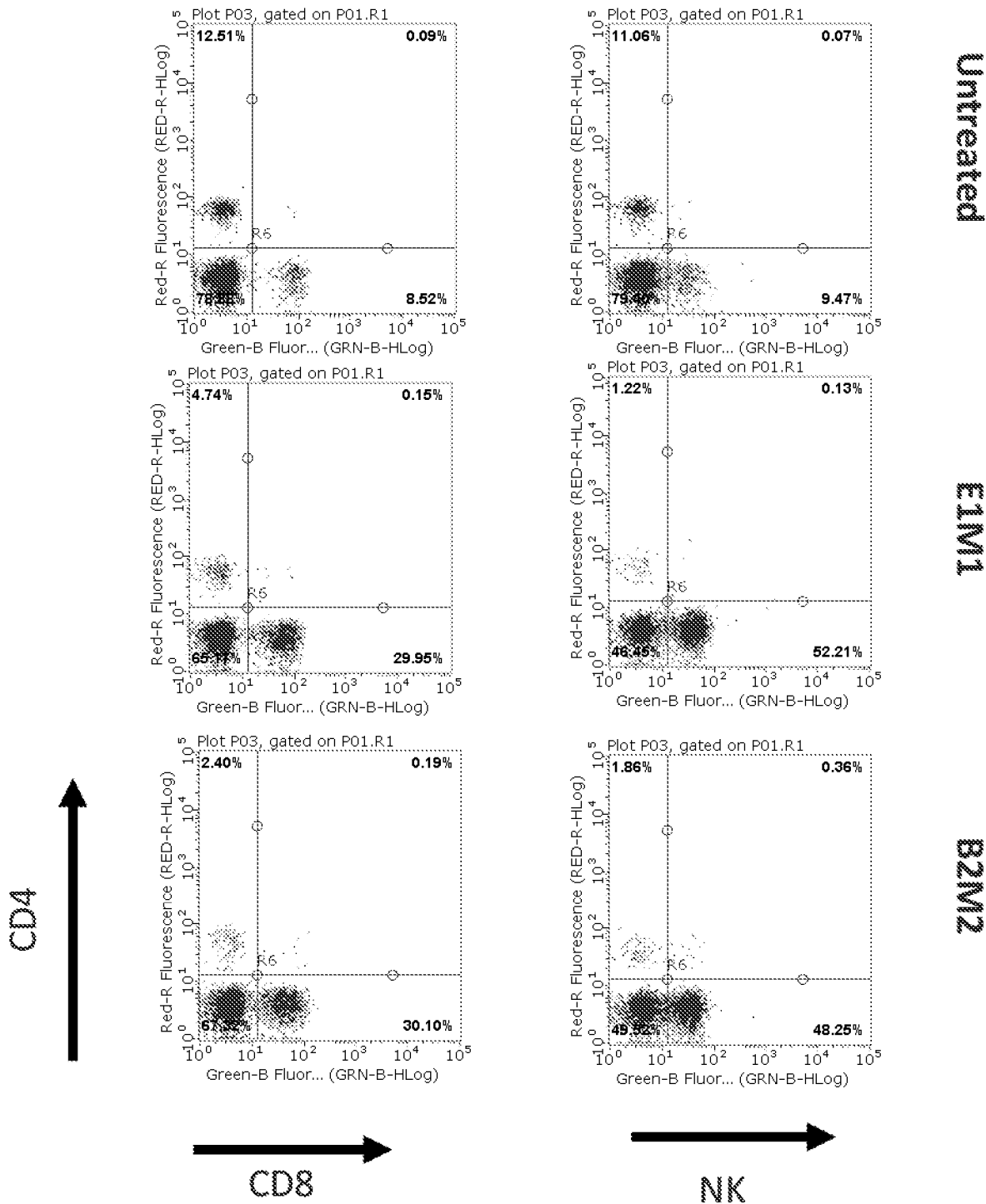
FIG. 13 shows ability of the various mutant forms of IL2 fusion protein of the present invention to differentially induce preferential proliferation of CD8+ T cells and NK cells over $T_{reg}$ cells.

FIG. 13 shows there is a large expansion of the NK and CD8+ T-cell compartments relative to the CDC compartment. The ability of the various mutant forms of the IL2 fusion proteins of the present invention to differentially induce preferential proliferation of CD8+ T-cells and NK cells over $T_{reg}$ cells indicates the great potential of the fusion proteins to improve the anti-tumor activity of checkpoint antibodies and their clinical applications in cancer treatment.

Example 10

For detection of tumor targeting by the fusion proteins, either syngeneic tumors (e.g. MC38 in B6 mice) or syngeneic tumors expressing human PDL1 were used. Typically, $1 \times 10^6$ tumor cells were implanted subcutaneously and allowed to grow until they reached 100 mm$^2$. The mice were injected with 0.1-10 mg/kg of the fusion protein. Tumor tissue and other organs were harvested at various time points and the accumulation of the fusion protein was determined by sandwich ELISA or immunohistochemistry. Alternatively, radioactively labeled proteins were used and detected using standard methods.

Sequences

Examples of sequences that form part of the fusion protein according to the present inventions are listed as follows.

Examples of the full-length sequences and variable region sequences for anti-PDL1 antibodies that block PD1-PDL1 interaction are as described below. The DNA sequences as examples are also described below. Other variations based on alternate codon usage of the DNA sequences are alternative under this invention.

```
PDL1 antibody
B2 Heavy chain
DNA sequence
                                                    (SEQ ID NO: 1)
ATGGAGTTTGGGCTGAGCTGGCTTTTTCTTGTCGCGATTCTTAAGGGTGTCCAGTGCGAAGTGCA

GCTGGTGGAGTCTGGGGGAGGCTTGGTACAGCCTGGAGGGTCCCTGAGACTCTCCTGTGCAGCC

TCTGGATTCACTTTTAGTGACTATGACATGATCTGGGTCCGCCAGGCTCCAGGCAAGGGGCTGG

AGTGGGTGGCAGTTATATCATATGATGGAAGTAATAAATACTATGCAGACTCCGTGAAGGGCCG

ATTCACCATCTCCAGAGACAATTCCAAGAACACGCTGTATCTGCAAATGAACAGCCTGAGAGCT

GAGGACACGGCTGTGTATTACTGTGCGAAAGAGTTCTTTGGTGCTTTTGATATCTGGGGCCAAG

GGACAATGGTCACCGTCTCTTCAGCTTCGACCAAGGGCCCATCGGTCTTCCCCCTGGCACCCTCC

TCCAAGAGCACCTCTGGGGGCACAGCGGCCCTGGGCTGCCTGGTCAAGGACTACTTCCCCGAAC

CGGTGACGGTGTCGTGGAACTCAGGCGCCCTGACCAGCGGCGTGCACACCTTCCCGGCTGTCCT

ACAGTCCTCAGGACTCTACTCCCTCAGCAGCGTGGTGACCGTGCCCTCCAGCAGCTTGGGCACC

CAGACCTACATCTGCAACGTGAATCACAAGCCCAGCAACACCAAGGTGGACAAGAAAGTTGAG

CCCAAATCTTGTGACAAAACTCACACATGCCCACCGTGCCCAGCACCTGAACTCCTGGGGGGAC

CGTCAGTCTTCCTCTTCCCCCCAAAACCCAAGGACACCCTCATGATCTCCCGGACCCCTGAGGTC

ACATGCGTGGTGGTGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAACAGCACGTACCGT

GTGGTCAGCGTCCTCACCGTCCTGCACCAGGACTGGCTGAATGGCAAGGAGTACAAGTGCAAG

GTCTCCAACAAAGCCCTCCCAGCCCCCATCGAGAAAACCATCTCCAAAGCCAAAGGGCAGCCCC

GAGAACCACAGGTGTACACCCTGCCCCCATCCCGCGAGGAGATGACCAAGAACCAGGTCAGCC
```

```
TGACCTGCCTGGTCAAAGGCTTCTATCCCAGCGACATCGCCGTGGAGTGGGAGAGCAATGGGCA

GCCGGAGAACAACTACAAGACCACGCCTCCCGTGCTGGACTCCGACGGCTCCTTCTTCCTCTAC

AGCAAGCTCACCGTGGACAAGAGCAGGTGGCAGCAGGGGAACGTCTTCTCATGCTCCGTGATG

CATGAGGCTCTGCACAACCACTACACGCAGAAGAGCCTCTCCCTGTCTCCGGGTAAATGA

Protein sequence
Full length
                                                      (SEQ ID NO: 2)
MEFGLSWLFLVAILKGVQCEVQLVESGGGLVQPGGSLRLSCAASGFTFSDYDMIWVRQAPGRGLE

WVAVISYDGSNKYYADSVKGRFTISRDNSKNTLYLQMNSLRAEDTAVYYCAKEFFGAFDIWGQGT

MVTVSSASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMHEALHNHYTQKSLSLSP

GK

Variable region
                                                      (SEQ ID NO: 3)
EVQLVESGGGLVQPGGSLRLSCAASGFTFSDYDMIWVRQAPGRGLEWVAVISYDGSNKYYADSVK

GRFTISRDNSKNTLYLQMNSLRAEDTAVYYCAKEFFGAFDIWGQGTMVTVSS

B2 Light chain
DNA sequence
                                                      (SEQ ID NO: 4)
ATGACTTGGACCCCACTCCTCTTCCTCACCCTCCTCCTCCACTGCACAGGAAGCTTATCCTCTTCT

GAGCTGACTCAGGACCCTGCTGTGTCGGTGGCCTTGGGACAGACAGTCACGATCACATGCCAAG

GAGACAGCCTCAATTACTATTATGCAAACTGGTTCCAGCTGAAGCCAGGGCAGGCCCCTGTACT

TGTCCTCTTTGGTAAAAACAACCGGCCCTCAGGGATCCCAGACCGATTCTCTGGCTCCTACTCGG

GAAGCACAGCTTCCTTGACCATCACTGGGGCTCAGGCGGAAGATGACGCTGACTATTACTGTAA

TTCGCGGGACAGCGGTGGTAATCCTTGGGTGTTCGGCGGAGGGACCAAGCTGACCGTCCTAGGT

CAACCCAAGGCTGCCCCCTCGGTCACTCTGTTCCCGCCCTCCTCTGAGGAGCTTCAAGCCAACA

AGGCCACACTGGTGTGTCTCATAAGTGACTTCTACCCGGGAGCCGTGACAGTGGCCTGGAAGGC

AGATAGCAGCCCCGTCAAGGCGGGAGTGGAGACCACCACACCCTCCAAACAAAGCAACAACAA

GTACGCGGCCAGCAGCTACCTGAGCCTGACGCCTGAGCAGTGGAAGTCCCACAGAAGCTACAG

CTGCCAGGTCACGCATGAAGGGAGCACCGTGGAGAAGACAGTGGCCCCTACAGAATGTTCATG

A

Protein sequence
Full length
                                                      (SEQ ID NO: 5)
MTWTPLLFLTLLLHCTGSLSSSELTQDPAVSVALGQTVTITCQGDSLNYYYANWFQLKPGQAPVLV

LFGKNNRPSGIPDRFSGSYSGSTASLTITGAQAEDDADYYCNSRDSGGNPWVFGGGTKLTVLGQPKA

APSVTLFPPSSEELQANKATLVCLISDFYPGAVTVAWKADSSPVKAGVETTTPSKQSNNKYAASSYL

SLTPEQWKSHRSYSCQVTHEGSTVEKTVAPTECS

Variable region
                                                      (SEQ ID NO: 6)
SSELTQDPAVSVALGQTVTITCQGDSLNYYYANWFQLKPGQAPVLVLFGKNNRPSGIPDRFSGSYSG

STASLTITGAQAEDDADYYCNSRDSGGNPWVFGGGTKLTVL
```

```
E1 Heavy chain
DNA sequence
                                                          (SEQ ID NO: 7)
ATGGAGTTTGGGCTGAGCTGGCTTTTTCTTGTCGCGATTCTTAAGGGTGTCCAGTGCCAAATCCA

GCTGGTACAATCTGGGGCTGAGGTGAAGATGCCTGGGGCCTCAGTGACGATTTCCTGCGAGGCG

TCTGGATACAACTTCATCAGCTACTATATACACTGGGTGCGACAGGCCCCTGGACAAGGCCTTG

AGTGGATGGGATTCGTCGTCCCTAGTGGTGGTGCCGCAGGCTACACACAGAAGTTCCAGGGCAG

ACTCACCGTGACCAGGGACACGTCCACGAGCACAGTCTACATGGACCTGAACAGCCTGACATCT

GACGACACGGCCGTGTATTACTGTGTGCGAGAAATGAGTGGTGGCTGGTTTGATTTCTGGGGCC

AGGGAACCCTGGTCACCGTCTCCTCGGCTTCGACCAAGGGCCCATCGGTCTTCCCCCTGGCACC

CTCCTCCAAGAGCACCTCTGGGGGCACAGCGGCCCTGGGCTGCCTGGTCAAGGACTACTTCCCC

GAACCGGTGACGGTGTCGTGGAACTCAGGCGCCCTGACCAGCGGCGTGCACACCTTCCCGGCTG

TCCTACAGTCCTCAGGACTCTACTCCCTCAGCAGCGTGGTGACCGTGCCCTCCAGCAGCTTGGGC

ACCCAGACCTACATCTGCAACGTGAATCACAAGCCCAGCAACACCAAGGTGGACAAGAAAGTT

GAGCCCAAATCTTGTGACAAAACTCACACATGCCCACCGTGCCCAGCACCTGAACTCCTGGGGG

GACCGTCAGTCTTCCTCTTCCCCCCAAAACCCAAGGACACCCTCATGATCTCCCGGACCCCTGAG

GTCACATGCGTGGTGGTGGACGTGAGCCACGAAGACCCTGAGGTCAAGTTCAACTGGTACGTGG

ACGGCGTGGAGGTGCATAATGCCAAGACAAAGCCGCGGGAGGAGCAGTACAACAGCACGTACC

GTGTGGTCAGCGTCCTCACCGTCCTGCACCAGGACTGGCTGAATGGCAAGGAGTACAAGTGCAA

GGTCTCCAACAAAGCCCTCCCAGCCCCCATCGAGAAAACCATCTCCAAAGCCAAAGGGCAGCC

CCGAGAACCACAGGTGTACACCCTGCCCCCATCCCGCGAGGAGATGACCAAGAACCAGGTCAG

CCTGACCTGCCTGGTCAAAGGCTTCTATCCCAGCGACATCGCCGTGGAGTGGGAGAGCAATGGG

CAGCCGGAGAACAACTACAAGACCACGCCTCCCGTGCTGGACTCCGACGGCTCCTTCTTCCTCT

ACAGCAAGCTCACCGTGGACAAGAGCAGGTGGCAGCAGGGGAACGTCTTCTCATGCTCCGTGA

TGCATGAGGCTCTGCACAACCACTACACGCAGAAGAGCCTCTCCCTGTCTCCGGGTAAATGA

Protein sequence
Full length
                                                          (SEQ ID NO: 8)
MEFGLSWLFLVAILKGVQCQIQLVQSGAEVKMPGASVTISCEASGYNFISYYIHWVRQAPGQGLEW

MGFVVPSGGAAGYTQKFQGRLTVTRDTSTSTVYMDLNSLTSDDTAVYYCVREMSGGWFDFWGQG

TLVTVSSASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMHEALHNHYTQKSLSLSP

GK

Variable region
                                                          (SEQ ID NO: 9)
SCEASGYNFISYYIHWVRQAPGQGLEWMGFVVPSGGAAGYTQKFQGRLTVTRDTSTSTVYMDLNS

LTSDDTAVYYCVREMSGGWFDFWGQGTLVTVSS

E1 Light chain
DNA sequence
                                                          (SEQ ID NO: 10)
ATGGACATGCGCGTGCCCGCCCAGCTGCTGGGCCTGCTGCTGCTGTGGTTCCCCGGCTCGCGAT

GCGACATCGTGATGACCCAGTCTCCATCCTCCCTGTCTGCATCTGTAGGAGACAGAGTCACCAT

CACTTGCCGGGCAAGTCAGGGCATTAGAAATGATTTAGGCTGGTATCAGCAAAAACCAGGGAA
```

-continued

```
AGCCCCTAAGCTCCTGATCTATGCTGCATCCACTTTGCAAAGTGGGGTCCCATCAAGGTTCAGC

GGCAGTGGATCTGGGACAGATTTCACTCTCACCATCAGCAGCCTGCAGGCTGAAGATGTGGCAG

TTTATTACTGTCAGCAATATTATAGTACTCCTCTCACTTTCGGCCCTGGGACCAAAGTGGATATC

AAACGTACGGTGGCTGCACCATCTGTCTTCATCTTCCCGCCATCTGATGAGCAGTTGAAATCTGG

AACTGCCTCTGTTGTGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCAGGACAGCAAGGAC

AGCACCTACAGCCTCAGCAGCACCCTGACGCTGAGCAAAGCAGACTACGAGAAACACAAAGTC

TACGCCTGCGAAGTCACCCATCAGGGCCTGAGCTCGCCCGTCACAAAGAGCTTCAACAGGGGA

GAGTGTTGA
```

Protein sequence
Full length (SEQ ID NO: 11)

```
MDMRVPAQLLGLLLLWFPGSRCDIVMTQSPSSLSASVGDRVTITCRASQGIRNDLGWYQQKPGKAP

KLLIYAASTLQSGVPSRFSGSGSGTDFTLTISSLQAEDVAVYYCQQYYSTPLTFGPGTKVDIKRTVAA

PSVFIFPPSDEQLKSGTASVVCLLNNFYPREAKVQWKVDNALQSGNSQESVTEQDSKDSTYSLSSTLT

LSKADYEKHKVYACEVTHQGLSSPVTKSFNRGEC
```

Variable region (SEQ ID NO: 12)

```
DIVMTQSPSSLSASVGDRVTITCRASQGIRNDLGWYQQKPGKAPKLLIYAASTLQSGVPSRFSGSGSG

TDFTLTISSLQAEDVAVYYCQQYYSTPLTFGPGTKVDIK
```

E3 Heavy chain
DNA sequence (SEQ ID NO: 13)

```
ATGGAGTTTGGGCTGAGCTGGCTTTTTCTTGTCGCGATTCTTAAGGGTGTCCAGTGCCAAATCCA

GCTGGTACAATCTGGGGCTGAGGTGAAGAAGCCTGGGTCCTCGGTGAAGGTCTCCTGCAAGGCT

TCTGGAGGCACCTTCAGCAGCTATGCTATCAGCTGGGTGCGACAGGCCCCTGGACAAGGGCTTG

AGTGGATGGGAGGGATCATCCCTATCTTTGGTACAGCAAACTACGCACAGAAGTTCCAGGGCAG

AGTCACGATTACCGCGGACAAATCCACGAGCACAGCCTACATGGAGCTGAGCAGCCTGAGATC

TGAGGACACGGCCGTGTATTACTGTGCCGGAGGGGGAGCAGTGGCGGACAATAGTTACTGGGG

CCAGGGAACCCTGGTCACCGTCTCCTCAGCTTCGACCAAGGGCCCATCGGTCTTCCCCCTGGCA

CCCTCCTCCAAGAGCACCTCTGGGGGCACAGCGGCCCTGGGCTGCCTGGTCAAGGACTACTTCC

CCGAACCGGTGACGGTGTCGTGGAACTCAGGCGCCCTGACCAGCGGCGTGCACACCTTCCCGGC

TGTCCTACAGTCCTCAGGACTCTACTCCCTCAGCAGCGTGGTGACCGTGCCCTCCAGCAGCTTGG

GCACCCAGACCTACATCTGCAACGTGAATCACAAGCCCAGCAACACCAAGGTGGACAAGAAAG

TTGAGCCCAAATCTTGTGACAAAACTCACACATGCCCACCGTGCCCAGCACCTGAACTCCTGGG

GGGACCGTCAGTCTTCCTCTTCCCCCCAAAACCCAAGGACACCCTCATGATCTCCCGGACCCCTG

AGGTCACATGCGTGGTGGTGGACGTGAGCCACGAAGACCCTGAGGTCAAGTTCAACTGGTACGT

GGACGGCGTGGAGGTGCATAATGCCAAGACAAAGCCGCGGGAGGAGCAGTACAACAGCACGT

ACCGTGTGGTCAGCGTCCTCACCGTCCTGCACCAGGACTGGCTGAATGGCAAGGAGTACAAGTG

CAAGGTCTCCAACAAAGCCCTCCCAGCCCCCATCGAGAAAACCATCTCCAAAGCCAAAGGGCA

GCCCCGAGAACCACAGGTGTACACCCTGCCCCCATCCCGCGAGGAGATGACCAAGAACCAGGT

CAGCCTGACCTGCCTGGTCAAAGGCTTCTATCCCAGCGACATCGCCGTGGAGTGGGAGAGCAAT
```

```
GGGCAGCCGGAGAACAACTACAAGACCACGCCTCCCGTGCTGGACTCCGACGGCTCCTTCTTCC

TCTACAGCAAGCTCACCGTGGACAAGAGCAGGTGGCAGCAGGGGAACGTCTTCTCATGCTCCGT

GATGCATGAGGCTCTGCACAACCACTACACGCAGAAGAGCCTCTCCCTGTCTCCGGGTAAATGA
```

Protein sequence
Full length
```
                                                       (SEQ ID NO: 14)
MEFGLSWLFLVAILKGVQCQIQLVQSGAEVKKPGSSVKVSCKASGGTFSSYAISWVRQAPGQGLEW

MGGIIPIFGTANYAQKFQGRVTITADKSTSTAYMELSSLRSEDTAVYYCAGGGAVADNSYWGQGTL

VTVSSASTKGPSVFPLAPSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMHEALHNHYTQKSLSLSP

GK
```

Variable region
```
                                                       (SEQ ID NO: 15)
QIQLVQSGAEVKKPGSSVKVSCKASGGTFSSYAISWVRQAPGQGLEWMGGIIPIFGTANYAQKFQGR

VTITADKSTSTAYMELSSLRSEDTAVYYCAGGGAVADNSYWGQGTLVTVSS
```

E3 Light chain
DNA sequence
```
                                                       (SEQ ID NO: 16)
ATGGACATGCGCGTGCCCGCCCAGCTGCTGGGCCTGCTGCTGCTGTGGTTCCCCGGCTCGCGAT

GCGACATCCGGATGACCCAGTCTCCATCCTCCCTGTCTGCATCTGTAGGAGACAGAGTCACCAT

CACTTGCCGGGCAAGTCAGGGCATTAGAAATGATTTAGGCTGGTATCAGCAGAAACCAGGGAA

AGCCCCTAAGCTCCTGATCTATGCTGCATCCAGTTTACAAAGTGGGGTCCCATCAAGGTTCAGC

GGCAGTGGATCTGGCACAGATTTCACTCTCACCATCAGCAGCCTGCAGCCTGAAGATTTTGCAA

CTTATTACTGTCTACAAGATTACAATTACCCTCGAACGTTCGGCCAAGGGACCAAGGTGGAAAT

CAAACGTACGGTGGCTGCACCATCTGTCTTCATCTTCCCGCCATCTGATGAGCAGTTGAAATCTG

GAACTGCCTCTGTTGTGTGCCTGCTGAATAACTTCTATCCCAGAGAGGCCAAAGTACAGTGGAA

GGTGGATAACGCCCTCCAATCGGGTAACTCCCAGGAGAGTGTCACAGAGCAGGACAGCAAGGA

CAGCACCTACAGCCTCAGCAGCACCCTGACGCTGAGCAAAGCAGACTACGAGAAACACAAAGT

CTACGCCTGCGAAGTCACCCATCAGGGCCTGAGCTCGCCCGTCACAAAGAGCTTCAACAGGGGA

GAGTGTTGA
```

Protein sequence
Full length
```
                                                       (SEQ ID NO: 17)
MDMRVPAQLLGLLLLWFPGSRCDIRMTQSPSSLSASVGDRVTITCRASQGIRNDLGWYQQKPGKAP

KLLIYAASSLQSGVPSRFSGSGSGTDFTLTISSLQPEDFATYYCLQDYNYPRTFGQGTKVEIKRTVAAP

SVFIFPPSDEQLKSGTASVVCLLNNFYPREAKVQWKVDNALQSGNSQESVTEQDSKDSTYSLSSTLT

LSKADYEKHKVYACEVTHQGLSSPVTKSFNRGEC
```

Variable region
```
                                                       (SEQ ID NO: 18)
DIRMTQSPSSLSASVGDRVTITCRASQGIRNDLGWYQQKPGKAPKLLIYAASSLQSGVPSRFSGSGSG

TDFTLTISSLQPEDFATYYCLQDYNYPRTFGQGTKVEIK
```

Example sequence of the linker is listed below:

```
            Ser-Gly linker
            Protein sequence
                            (SEQ ID NO: 19)
            GGGGSGGGGSGGGGSGGGGS
```

Example sequence of (a) IL2WT (Wild type IL2 sequence); (b) IL2Del (20 amino acid deletion); and (c) IL2M1-MNew (MutIL2: the mutants that have the desired features, combinations of these mutations could also be used) are listed below:

```
IL2 mutants
IL2WT
DNA sequence
                                                   (SEQ ID NO: 20)
GGCGCCCCCACATCCTCCAGCACCAAGAAGACCCAGCTGCAGCTGGAGCATCTGCTGCTGGATC

TGCAGATGATTTTAAACGGCATCAACAACTACAAGAACCCCAAGCTGACCCGGATGCTGACCTT

CAAGTTCTACATGCCCAAGAAGGCCACCGAGCTGAAGCATTTACAGTGTCTGGAGGAAGAGCT

GAAGCCTTTAGAGGAAGTGCTCAATTTAGCCCAGTCCAAGAACTTCCATTTAAGGCCACGTGAT

TTAATCTCCAACATCAACGTGATCGTGCTGGAGCTGAAGGGCTCCGAGACCACCTTCATGTGCG

AGTACGCCGACGAGACCGCCACCATCGTGGAGTTTTTAAATCGTTGGATCACCTTCTGCCAGAG

CATCATCTCCACTTTAACCTGA

Protein sequence
                                                   (SEQ ID NO: 21)
GAPTSSSTKKTQLQLEHLLLDLQMILNGINNYKNPKLTRMLTFKFYMPKKATELKHLQCLEEELKPL

EEVLNLAQSKNFHLRPRDLISNINVIVLELKGSETTFMCEYADETATIVEFLNRWITFCQSIISTLT

IL2Del
DNA sequence
                                                   (SEQ ID NO: 22)
GGCGCCCCCACATCCTCCAGCACCAAGAAGACCCAGCTGCAGCTGGAGCATCTGCTGCTGGATC

TGCAGATGATTTTAAACGGCATCAACGCCACCGAGCTGAAGCATTTACAGTGTCTGGAGGAAGA

GCTGAAGCCTTTAGAGGAAGTGCTCAATTTAGCCCAGTCCAAGAACTTCCATTTAAGGCCACGT

GATTTAATCTCCAACATCAACGTGATCGTGCTGGAGCTGAAGGGCTCCGAGACCACCTTCATGT

GCGAGTACGCCGACGAGACCGCCACCATCGTGGAGTTTTTAAATCGTTGGATCACCTTCTGCCA

GAGCATCATCTCCACTTTAACCTGA

Protein sequence
                                                   (SEQ ID NO: 23)
GAPTSSSTKKTQLQLEHLLLDLQMILNGINATELKHLQCLEEELKPLEEVLNLAQSKNFHLRPRDLIS

NINVIVLELKGSETTFMCEYADETATIVEFLNRWITFCQSIISTLT

IL2M1: F42K, Y45R
DNA sequence
                                                   (SEQ ID NO: 24)
GGCGCCCCCACATCCTCCAGCACCAAGAAGACCCAGCTGCAGCTGGAGCATCTGCTGCTGGATC

TGCAGATGATTTTAAACGGCATCAACAACTACAAGAACCCCAAGCTGACCCGGATGCTGACCAA

GAAGTTCCGCATGCCCAAGAAGGCCACCGAGCTGAAGCATTTACAGTGTCTGGAGGAAGAGCT

GAAGCCTTTAGAGGAAGTGCTCAATTTAGCCCAGTCCAAGAACTTCCATTTAAGGCCACGTGAT

TTAATCTCCAACATCAACGTGATCGTGCTGGAGCTGAAGGGCTCCGAGACCACCTTCATGTGCG

AGTACGCCGACGAGACCGCCACCATCGTGGAGTTTTTAAATCGTTGGATCACCTTCTGCCAGAG

CATCATCTCCACTTTAACCTGA
```

-continued

Protein sequence
(SEQ ID NO: 25)
GAPTSSSTKKTQLQLEHLLLDLQMILNGINNYKNPKLTRMLTKKFRMPKKATELKHLQCLEEELKPL

EEVLNLAQSKNFHLRPRDLISNINVIVLELKGSETTFMCEYADETATIVEFLNRWITFCQSIISTLT

IL2M2: F42A, Y45R
DNA sequence
(SEQ ID NO: 26)
GGCGCCCCCACATCCTCCAGCACCAAGAAGACCCAGCTGCAGCTGGAGCATCTGCTGCTGGATC

TGCAGATGATTTTAAACGGCATCAACAACTACAAGAACCCCAAGCTGACCCGGATGCTGACCGC

CAAGTTCCGCATGCCCAAGAAGGCCACCGAGCTGAAGCATTTACAGTGTCTGGAGGAAGAGCT

GAAGCCTTTAGAGGAAGTGCTCAATTTAGCCCAGTCCAAGAACTTCCATTTAAGGCCACGTGAT

TTAATCTCCAACATCAACGTGATCGTGCTGGAGCTGAAGGGCTCCGAGACCACCTTCATGTGCG

AGTACGCCGACGAGACCGCCACCATCGTGGAGTTTTTAAATCGTTGGATCACCTTCTGCCAGAG

CATCATCTCCACTTTAACCTGA

Protein sequence
(SEQ ID NO: 27)
GAPTSSSTKKTQLQLEHLLLDLQMILNGINNYKNPKLTRMLTAKFRMPKKATELKHLQCLEEELKPL

EEVLNLAQSKNFHLRPRDLISNINVIVLELKGSETTFMCEYADETATIVEFLNRWITFCQSIISTLT

IL2M3: E62R
DNA sequence
(SEQ ID NO: 28)
GGCGCCCCCACATCCTCCAGCACCAAGAAGACCCAGCTGCAGCTGGAGCATCTGCTGCTGGATC

TGCAGATGATTTTAAACGGCATCAACAACTACAAGAACCCCAAGCTGACCCGGATGCTGACCTT

CAAGTTCTACATGCCCAAGAAGGCCACCGAGCTGAAGCATTTACAGTGTCTGGAGGAAAGGCT

GAAGCCTTTAGAGGAAGTGCTCAATTTAGCCCAGTCCAAGAACTTCCATTTAAGGCCACGTGAT

TTAATCTCCAACATCAACGTGATCGTGCTGGAGCTGAAGGGCTCCGAGACCACCTTCATGTGCG

AGTACGCCGACGAGACCGCCACCATCGTGGAGTTTTTAAATCGTTGGATCACCTTCTGCCAGAG

CATCATCTCCACTTTAACCTGA

Protein sequence
(SEQ ID NO: 29)
GAPTSSSTKKTQLQLEHLLLDLQMILNGINNYKNPKLTRMLTFKFYMPKKATELKHLQCLEERLKPL

EEVLNLAQSKNFHLRPRDLISNINVIVLELKGSETTFMCEYADETATIVEFLNRWITFCQSIISTLT

IL2M4: R38A, F42A
DNA sequence
(SEQ ID NO: 30)
GGCGCCCCCACATCCTCCAGCACCAAGAAGACCCAGCTGCAGCTGGAGCATCTGCTGCTGGATC

TGCAGATGATTTTAAACGGCATCAACAACTACAAGAACCCCAAGCTGACCGCCATGCTGACCGC

CAAGTTCTACATGCCCAAGAAGGCCACCGAGCTGAAGCATTTACAGTGTCTGGAGGAAGAGCT

GAAGCCTTTAGAGGAAGTGCTCAATTTAGCCCAGTCCAAGAACTTCCATTTAAGGCCACGTGAT

TTAATCTCCAACATCAACGTGATCGTGCTGGAGCTGAAGGGCTCCGAGACCACCTTCATGTGCG

AGTACGCCGACGAGACCGCCACCATCGTGGAGTTTTTAAATCGTTGGATCACCTTCTGCCAGAG

CATCATCTCCACTTTAACCTGA

Protein sequence
(SEQ ID NO: 31)
GAPTSSSTKKTQLQLEHLLLDLQMILNGINNYKNPKLTAMLTAKFYMPKKATELKHLQCLEEELKPL

EEVLNLAQSKNFHLRPRDLISNINVIVLELKGSETTFMCEYADETATIVEFLNRWITFCQSIISTLT

-continued

IL2M5: R38A, F42A, Y45A, E62A, C125S
DNA sequence
(SEQ ID NO: 32)
GGAGCTCCTACCTCCTCCTCCACCAAGAAGACCCAGCTCCAGCTGGAACATTTACTGCTGGATTT

ACAGATGATTTTAAACGGCATCAACAATTACAAGAACCCCAAGCTGACCGCCATGCTGACCGCC

AAGTTTGCCATGCCCAAGAAGGCCACCGAGCTGAAGCATTTACAGTGTTTAGAGGAGGCTTTAA

AGCCTTTAGAGGAGGTGCTGAATTTAGCCCAGTCCAAGAACTTCCATTTAAGGCCCCGGGATTT

AATCTCCAACATCAACGTGATCGTGCTGGAACTGAAGGGCAGCGAGACCACCTTTATGAGCGAA

TACGCCGACGAGACCGCCACCATCGTGGAGTTTTTAAATCGTTGGATCACCTTCTGCCAGTCCAT

CATCTCCACTTTAACCTGA

Protein sequence
(SEQ ID NO: 33)
GAPTSSSTKKTQLQLEHLLLDLQMILNGINNYKNPKLTAMLTAKFAMPKKATELKHLQCLEEALKP

LEEVLNLAQSKNFHLRPRDLISNINVIVLELKGSETTFMSEYADETATIVEFLNRWITFSQSIISTLT

IL2M6: R38A, F42K
DNA sequence
(SEQ ID NO: 34)
GGCGCCCCCACATCCTCCAGCACCAAGAAGACCCAGCTGCAGCTGGAGCATCTGCTGCTGGATC

TGCAGATGATTTTAAACGGCATCAACAACTACAAGAACCCCAAGCTGACCGCCATGCTGACCAA

GAAGTTCTACATGCCCAAGAAGGCCACCGAGCTGAAGCATTTACAGTGTCTGGAGGAAGAGCT

GAAGCCTTTAGAGGAAGTGCTCAATTTAGCCCAGTCCAAGAACTTCCATTTAAGGCCACGTGAT

TTAATCTCCAACATCAACGTGATCGTGCTGGAGCTGAAGGGCTCCGAGACCACCTTCATGTGCG

AGTACGCCGACGAGACCGCCACCATCGTGGAGTTTTTAAATCGTTGGATCACCTTCTGCCAGAG

CATCATCTCCACTTTAACCTGA

Protein sequence
(SEQ ID NO: 35)
GAPTSSSTKKTQLQLEHLLLDLQMILNGINNYKNPKLTAMLTKKFYMPKKATELKHLQCLEEELKPL

EEVLNLAQSKNFHLRPRDLISNINVIVLELKGSETTFMCEYADETATIVEFLNRWITFCQSIISTLT

IL2M7: R38A, F42A, E62R
DNA sequence
(SEQ ID NO: 36)
GGCGCCCCCACATCCTCCAGCACCAAGAAGACCCAGCTGCAGCTGGAGCATCTGCTGCTGGATC

TGCAGATGATTTTAAACGGCATCAACAACTACAAGAACCCCAAGCTGACCGCCATGCTGACCGC

CAAGTTCTACATGCCCAAGAAGGCCACCGAGCTGAAGCATTTACAGTGTCTGGAGGAAAGGCT

GAAGCCTTTAGAGGAAGTGCTCAATTTAGCCCAGTCCAAGAACTTCCATTTAAGGCCACGTGAT

TTAATCTCCAACATCAACGTGATCGTGCTGGAGCTGAAGGGCTCCGAGACCACCTTCATGTGCG

AGTACGCCGACGAGACCGCCACCATCGTGGAGTTTTTAAATCGTTGGATCACCTTCTGCCAGAG

CATCATCTCCACTTTAACCTGA

Protein sequence
(SEQ ID NO: 37)
GAPTSSSTKKTQLQLEHLLLDLQMILNGINNYKNPKLTAMLTAKFYMPKKATELKHLQCLEERLKPL

EEVLNLAQSKNFHLRPRDLISNINVIVLELKGSETTFMCEYADETATIVEFLNRWITFCQSIISTLT

IL2M8: F42K, Y45R, E62R
DNA sequence
(SEQ ID NO: 38)
GGCGCCCCCACATCCTCCAGCACCAAGAAGACCCAGCTGCAGCTGGAGCATCTGCTGCTGGATC

TGCAGATGATTTTAAACGGCATCAACAACTACAAGAACCCCAAGCTGACCCGGATGCTGACCAA

GAAGTTCCGCATGCCCAAGAAGGCCACCGAGCTGAAGCATTTACAGTGTCTGGAGGAAAGGCT

GAAGCCTTTAGAGGAAGTGCTCAATTTAGCCCAGTCCAAGAACTTCCATTTAAGGCCACGTGAT

```
TTAATCTCCAACATCAACGTGATCGTGCTGGAGCTGAAGGGCTCCGAGACCACCTTCATGTGCG

AGTACGCCGACGAGACCGCCACCATCGTGGAGTTTTTAAATCGTTGGATCACCTTCTGCCAGAG

CATCATCTCCACTTTAACCTGA
```

Protein sequence (SEQ ID NO: 39)

```
GAPTSSSTKKTQLQLEHLLLDLQMILNGINNYKNPKLTRMLTKKFRMPKKATELKHLQCLEERLKPL

EEVLNLAQSKNFHLRPRDLISNINVIVLELKGSETTFMCEYADETATIVEFLNRWITFCQSIISTLT
```

IL2M9: F42A, Y45R, E62R
DNA sequence (SEQ ID NO: 40)

```
GGCGCCCCCACATCCTCCAGCACCAAGAAGACCCAGCTGCAGCTGGAGCATCTGCTGCTGGATC

TGCAGATGATTTTAAACGGCATCAACAACTACAAGAACCCCAAGCTGACCCGGATGCTGACCGC

CAAGTTCCGCATGCCCAAGAAGGCCACCGAGCTGAAGCATTTACAGTGTCTGGAGGAAAGGCT

GAAGCCTTTAGAGGAAGTGCTCAATTTAGCCCAGTCCAAGAACTTCCATTTAAGGCCACGTGAT

TTAATCTCCAACATCAACGTGATCGTGCTGGAGCTGAAGGGCTCCGAGACCACCTTCATGTGCG

AGTACGCCGACGAGACCGCCACCATCGTGGAGTTTTTAAATCGTTGGATCACCTTCTGCCAGAG

CATCATCTCCACTTTAACCTGA
```

Protein sequence (SEQ ID NO: 41)

```
GAPTSSSTKKTQLQLEHLLLDLQMILNGINNYKNPKLTRMLTAKFRMPKKATELKHLQCLEERLKPL

EEVLNLAQSKNFHLRPRDLISNINVIVLELKGSETTFMCEYADETATIVEFLNRWITFCQSIISTLT
```

IL2M10: R38A, F42K, E62R
DNA sequence (SEQ ID NO: 42)

```
GGCGCCCCCACATCCTCCAGCACCAAGAAGACCCAGCTGCAGCTGGAGCATCTGCTGCTGGATC

TGCAGATGATTTTAAACGGCATCAACAACTACAAGAACCCCAAGCTGACCGCCATGCTGACCAA

GAAGTTCTACATGCCCAAGAAGGCCACCGAGCTGAAGCATTTACAGTGTCTGGAGGAAAGGCT

GAAGCCTTTAGAGGAAGTGCTCAATTTAGCCCAGTCCAAGAACTTCCATTTAAGGCCACGTGAT

TTAATCTCCAACATCAACGTGATCGTGCTGGAGCTGAAGGGCTCCGAGACCACCTTCATGTGCG

AGTACGCCGACGAGACCGCCACCATCGTGGAGTTTTTAAATCGTTGGATCACCTTCTGCCAGAG

CATCATCTCCACTTTAACCTGA
```

Protein sequence (SEQ ID NO: 43)

```
GAPTSSSTKKTQLQLEHLLLDLQMILNGINNYKNPKLTAMLTKKFYMPKKATELKHLQCLEERLKPL

EEVLNLAQSKNFHLRPRDLISNINVIVLELKGSETTFMCEYADETATIVEFLNRWITFCQSIISTLT
```

IL2DelM3: Del, E62R
DNA sequence (SEQ ID NO: 44)

```
GGCGCCCCCACATCCTCCAGCACCAAGAAGACCCAGCTGCAGCTGGAGCATCTGCTGCTGGATC

TGCAGATGATTTTAAACGGCATCAACGCCACCGAGCTGAAGCATTTACAGTGTCTGGAGGAAAG

GCTGAAGCCTTTAGAGGAAGTGCTCAATTTAGCCCAGTCCAAGAACTTCCATTTAAGGCCACGT

GATTTAATCTCCAACATCAACGTGATCGTGCTGGAGCTGAAGGGCTCCGAGACCACCTTCATGT

GCGAGTACGCCGACGAGACCGCCACCATCGTGGAGTTTTTAAATCGTTGGATCACCTTCTGCCA

GAGCATCATCTCCACTTTAACCTGA
```

Protein sequence (SEQ ID NO: 45)

```
GAPTSSSTKKTQLQLEHLLLDLQMILNGINATELKHLQCLEERLKPLEEVLNLAQSKNFHLRPRDLIS

NINVIVLELKGSETTFMCEYADETATIVEFLNRWITFCQSIISTLT
```

-continued

IL2M3K: E62K
DNA sequence
(SEQ ID NO: 46)
GGCGCCCCCACATCCTCCAGCACCAAGAAGACCCAGCTGCAGCTGGAGCATCTGCTGCTGGATC

TGCAGATGATTTTAAACGGCATCAACAACTACAAGAACCCCAAGCTGACCCGGATGCTGACCTT

CAAGTTCTACATGCCCAAGAAGGCCACCGAGCTGAAGCATTTACAGTGTCTGGAGGAAAAGCT

GAAGCCTTTAGAGGAAGTGCTCAATTTAGCCCAGTCCAAGAACTTCCATTTAAGGCCACGTGAT

TTAATCTCCAACATCAACGTGATCGTGCTGGAGCTGAAGGGCTCCGAGACCACCTTCATGTGCG

AGTACGCCGACGAGACCGCCACCATCGTGGAGTTTTTAAATCGTTGGATCACCTTCTGCCAGAG

CATCATCTCCACTTTAACCTGA

Protein sequence
(SEQ ID NO: 47)
GAPTSSSTKKTQLQLEHLLLDLQMILNGINNYKNPKLTRMLTFKFYMPKKATELKHLQCLEEKLKPL

EEVLNLAQSKNFHLRPRDLISNINVIVLELKGSETTFMCEYADETATIVEFLNRWITFCQSIISTLT

IL2M6K: R38A, F42K, E62K
DNA sequence
(SEQ ID NO: 48)
GGCGCCCCCACATCCTCCAGCACCAAGAAGACCCAGCTGCAGCTGGAGCATCTGCTGCTGGATC

TGCAGATGATTTTAAACGGCATCAACAACTACAAGAACCCCAAGCTGACCGCCATGCTGACCAA

GAAGTTCTACATGCCCAAGAAGGCCACCGAGCTGAAGCATTTACAGTGTCTGGAGGAAAAGCT

GAAGCCTTTAGAGGAAGTGCTCAATTTAGCCCAGTCCAAGAACTTCCATTTAAGGCCACGTGAT

TTAATCTCCAACATCAACGTGATCGTGCTGGAGCTGAAGGGCTCCGAGACCACCTTCATGTGCG

AGTACGCCGACGAGACCGCCACCATCGTGGAGTTTTTAAATCGTTGGATCACCTTCTGCCAGAG

CATCATCTCCACTTTAACCTGA

Protein sequence
(SEQ ID NO: 49)
GAPTSSSTKKTQLQLEHLLLDLQMILNGINNYKNPKLTAMLTKKFYMPKKATELKHLQCLEEKLKP

LEEVLNLAQSKNFHLRPRDLISNINVIVLELKGSETTFMCEYADETATIVEFLNRWITFCQSIISTLT

IL2M7K: R38A, F42A, E62K
DNA sequence
(SEQ ID NO: 50)
GGCGCCCCCACATCCTCCAGCACCAAGAAGACCCAGCTGCAGCTGGAGCATCTGCTGCTGGATC

TGCAGATGATTTTAAACGGCATCAACAACTACAAGAACCCCAAGCTGACCGCCATGCTGACCGC

CAAGTTCTACATGCCCAAGAAGGCCACCGAGCTGAAGCATTTACAGTGTCTGGAGGAAAAGCT

GAAGCCTTTAGAGGAAGTGCTCAATTTAGCCCAGTCCAAGAACTTCCATTTAAGGCCACGTGAT

TTAATCTCCAACATCAACGTGATCGTGCTGGAGCTGAAGGGCTCCGAGACCACCTTCATGTGCG

AGTACGCCGACGAGACCGCCACCATCGTGGAGTTTTTAAATCGTTGGATCACCTTCTGCCAGAG

CATCATCTCCACTTTAACCTGA

Protein sequence
(SEQ ID NO: 51)
GAPTSSSTKKTQLQLEHLLLDLQMILNGINNYKNPKLTAMLTAKFYMPKKATELKHLQCLEEKLKP

LEEVLNLAQSKNFHLRPRDLISNINVIVLELKGSETTFMCEYADETATIVEFLNRWITFCQSIISTLT

IL2M8K: F42K, Y45R, E62K
DNA sequence
(SEQ ID NO: 52)
GGCGCCCCCACATCCTCCAGCACCAAGAAGACCCAGCTGCAGCTGGAGCATCTGCTGCTGGATC

TGCAGATGATTTTAAACGGCATCAACAACTACAAGAACCCCAAGCTGACCCGGATGCTGACCAA

GAAGTTCCGCATGCCCAAGAAGGCCACCGAGCTGAAGCATTTACAGTGTCTGGAGGAAAAGCT

GAAGCCTTTAGAGGAAGTGCTCAATTTAGCCCAGTCCAAGAACTTCCATTTAAGGCCACGTGAT

```
                                                               -continued
TTAATCTCCAACATCAACGTGATCGTGCTGGAGCTGAAGGGCTCCGAGACCACCTTCATGTGCG

AGTACGCCGACGAGACCGCCACCATCGTGGAGTTTTTAAATCGTTGGATCACCTTCTGCCAGAG

CATCATCTCCACTTTAACCTGA

Protein sequence
                                                                        (SEQ ID NO: 53)
GAPTSSSTKKTQLQLEHLLLDLQMILNGINNYKNPKLTRMLTKKFRMPKKATELKHLQCLEEKLKPL

EEVLNLAQSKNFHLRPRDLISNINVIVLELKGSETTFMCEYADETATIVEFLNRWITFCQSIISTLT

IL2M9K: F42A, Y45R, E62K
DNA sequence
                                                                        (SEQ ID NO: 54)
GGCGCCCCCACATCCTCCAGCACCAAGAAGACCCAGCTGCAGCTGGAGCATCTGCTGCTGGATC

TGCAGATGATTTTAAACGGCATCAACAACTACAAGAACCCCAAGCTGACCCGGATGCTGACCGC

CAAGTTCCGCATGCCCAAGAAGGCCACCGAGCTGAAGCATTTACAGTGTCTGGAGGAAAAGCT

GAAGCCTTTAGAGGAAGTGCTCAATTTAGCCCAGTCCAAGAACTTCCATTTAAGGCCACGTGAT

TTAATCTCCAACATCAACGTGATCGTGCTGGAGCTGAAGGGCTCCGAGACCACCTTCATGTGCG

AGTACGCCGACGAGACCGCCACCATCGTGGAGTTTTTAAATCGTTGGATCACCTTCTGCCAGAG

CATCATCTCCACTTTAACCTGA

Protein sequence
                                                                        (SEQ ID NO: 55)
GAPTSSSTKKTQLQLEHLLLDLQMILNGINNYKNPKLTRMLTAKFRMPKKATELKHLQCLEEKLKPL

EEVLNLAQSKNFHLRPRDLISNINVIVLELKGSETTFMCEYADETATIVEFLNRWITFCQSIISTLT

IL2MNew: K35E R38A F42A E61K L72G
DNA sequence
                                                                        (SEQ ID NO: 56)
GGCGCCCCCACATCCTCCAGCACCAAGAAGACCCAGCTGCAGCTGGAGCATCTGCTGCTGGATC

TGCAGATGATTTTAAACGGCATCAACAACTACAAGAACCCCGAGCTGACCGCCATGCTGACCGC

CAAGTTCTACATGCCCAAGAAGGCCACCGAGCTGAAGCATTTACAGTGTCTGGAGAAAGAGCT

GAAGCCTTTAGAGGAAGTGCTCAATGGCGCCCAGTCCAAGAACTTCCATTTAAGGCCACGTGAT

TTAATCTCCAACATCAACGTGATCGTGCTGGAGCTGAAGGGCTCCGAGACCACCTTCATGTGCG

AGTACGCCGACGAGACCGCCACCATCGTGGAGTTTTTAAATCGTTGGATCACCTTCTGCCAGAG

CATCATCTCCACTTTAACCTGA

Protein sequence
                                                                        (SEQ ID NO: 57)
GAPTSSSTKKTQLQLEHLLLDLQMILNGINNYKNPELTAMLTAKFYMPKKATELKHLQCLEKELKPL

EEVLNGAQSKNFHLRPRDLISNINVIVLELKGSETTFMCEYADETATIVEFLNRWITFCQSIISTLT
```

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Throughout this application, various publications, patents, and/or patent applications are referenced in order to more fully describe the state of the art to which this invention pertains. The disclosures of these publications, patents, and/or patent applications are herein incorporated by reference in their entireties to the same extent as if each independent publication, patent, and/or patent application was specifically and individually indicated to be incorporated by reference.

The invention claimed is:

1. A fusion protein, comprising a therapeutic protein connected to a mutant Interleukin-2 (IL2) polypeptide, wherein the therapeutic protein is an entire anti-PDL1 antibody, and wherein the mutant IL2 polypeptide comprises an amino acid sequence identical to SEQ ID NO: 25 or SEQ ID NO: 27.

2. The fusion protein of claim 1, wherein the entire anti-PDL1 antibody comprises a pair of heavy chains and a pair of light chains, and wherein the fusion protein comprises two mutant IL2 polypeptides, each mutant IL2 polypeptide connected to one of the C-terminals of the heavy chains.

3. The fusion protein of claim 2, wherein each mutant IL2 polypeptide is connected to the corresponding C-terminal of the heavy chains through a linker sequence.

4. The fusion protein of claim 3, wherein the linker sequence is a serine-glycine linker.

5. The fusion protein of claim 4, wherein the linker sequence is SEQ ID NO: 19.

6. The fusion protein of claim 1, wherein the anti-PDL1 antibody has one or more of the following features: (a) it binds PDL1 with Kd<100 nM to both purified protein as well as protein expressed on cell surface; (b) it blocks PDL1-PD1 interaction in vitro; and/or (c) it de-represses PDL1-mediated repression of effector T cells in activated PBMC cultures.

7. The fusion protein of claim 1, wherein the anti-PDL1 antibody is an antibody of any available isotype or any mutant forms of Fc region that mediates or enhances ADCC and/or CDC function.

8. The fusion protein of claim 1, wherein the anti-PDL1 antibody is an antibody of IgG1 isotype.

9. The fusion protein of claim 1, wherein the anti-PDL1 antibody comprises a heavy chain variable region and a light chain variable region where their respective sequences consist of pairings selected from the group consisting of: (a) SEQ ID NO: 3 and SEQ ID NO: 6; (b) SEQ ID NO: 9 and SEQ ID NO: 12; and (c) SEQ ID NO: 15 and SEQ ID NO: 18.

10. The fusion protein of claim 9, wherein the anti-PDL1 antibody comprises a heavy chain and a light chain where their respective sequences are at least 95% identical to the pairings selected from the group consisting of: (a) SEQ ID NO: 2 and SEQ ID NO: 5; (b) SEQ ID NO: 8 and SEQ ID NO: 11; and (c) SEQ ID NO: 14 and SEQ ID NO: 17.

11. A pharmaceutical composition comprising the fusion protein of claim 1, and a pharmaceutically acceptable excipient, carrier or diluent.

12. A nucleic acid molecule that encodes the fusion protein of claim 1, wherein the nucleic acid molecule is a DNA molecule or RNA molecule.

13. A mammalian expression system that produces the fusion protein of claim 1.

14. A mutant IL2 polypeptide that is less selective towards a high-affinity receptor of a wild type IL2, wherein the mutant IL2 polypeptide comprises an amino acid sequence identical to a sequence selected from the group consisting of SEQ ID NO: 25, and SEQ ID NO: 27.

\* \* \* \* \*

SEQUENCE LISTING

```
<160> NUMBER OF SEQ ID NOS: 57

<210> SEQ ID NO 1
<211> LENGTH: 1401
<212> TYPE: DNA
<213> ORGANISM: Artificial Sequence
```

<220> FEATURE:
<223> OTHER INFORMATION: DNA sequence of PDL1 antibody B2 heavy chain

<400> SEQUENCE: 1

```
atggagtttg ggctgagctg gcttttctt gtcgcgattc ttaagggtgt ccagtgcgaa      60
gtgcagctgg tggagtctgg gggaggcttg gtacagcctg agggtccct gagactctcc    120
tgtgcagcct ctggattcac ttttagtgac tatgacatga tctgggtccg ccaggctcca    180
ggcaaggggc tggagtgggt ggcagttata tcatatgatg aagtaataa atactatgca    240
gactccgtga agggccgatt caccatctcc agagacaatt ccaagaacac gctgtatctg    300
caaatgaaca gcctgagagc tgaggacacg gctgtgtatt actgtgcgaa agagttcttt    360
ggtgcttttg atatctgggg ccaagggaca atggtcaccg tctcttcagc ttcgaccaag    420
ggcccatcgg tcttcccct ggcacccctcc tccaagagca cctctggggg cacagcggcc    480
ctgggctgcc tggtcaagga ctacttcccc gaaccggtga cggtgtcgtg aactcaggc    540
gccctgacca gcggcgtgca caccttcccg gctgtcctac agtcctcagg actctactcc    600
ctcagcagcg tggtgaccgt gccctccagc agcttgggca cccagaccta catctgcaac    660
gtgaatcaca gcccagcaa caccaaggtg gacaagaaag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggaccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca caaagccct cccagccccc atcgagaaaa ccatctccaa agccaaaggg   1080
cagccccgag aaccacaggt gtacaccctg cccccatccc gcgaggagat gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct cctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaatg a                                              1401
```

<210> SEQ ID NO 2
<211> LENGTH: 466
<212> TYPE: PRT
<213> ORGANISM: Artificial Sequence
<220> FEATURE:
<223> OTHER INFORMATION: full length protein sequence of PDL1 antibody
      B2 heavy chain

<400> SEQUENCE: 2

```
Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Tyr Asp Met Ile Trp Val Arg Gln Ala Pro Gly Lys Gly Leu
    50                  55                  60

Glu Trp Val Ala Val Ile Ser Tyr Asp Gly Ser Asn Lys Tyr Tyr Ala
65                  70                  75                  80
```

-continued

```
Asp Ser Val Lys Gly Arg Phe Thr Ile Ser Arg Asp Asn Ser Lys Asn
             85                  90                  95

Thr Leu Tyr Leu Gln Met Asn Ser Leu Arg Ala Glu Asp Thr Ala Val
        100                 105                 110

Tyr Tyr Cys Ala Lys Glu Phe Phe Gly Ala Phe Asp Ile Trp Gly Gln
        115                 120                 125

Gly Thr Met Val Thr Val Ser Ser Ala Ser Thr Lys Gly Pro Ser Val
        130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
        210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
        290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
                340                 345                 350

Lys Thr Ile Ser Lys Ala Lys Gly Gln Pro Arg Glu Pro Gln Val Tyr
            355                 360                 365

Thr Leu Pro Pro Ser Arg Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
450                 455                 460

Gly Lys
465

<210> SEQ ID NO 3
<211> LENGTH: 117
<212> TYPE: PRT
```

<213> ORGANISM: Artificial Sequence
<220> FEATURE:
<223> OTHER INFORMATION: variable region protein sequence of PDL1 antibody B2 heavy chain

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ile Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Phe Phe Gly Ala Phe Asp Ile Trp Gly Gln Gly Thr Met
            100                 105                 110

Val Thr Val Ser Ser
        115
```

<210> SEQ ID NO 4
<211> LENGTH: 705
<212> TYPE: DNA
<213> ORGANISM: Artificial Sequence
<220> FEATURE:
<223> OTHER INFORMATION: DNA sequence of PDL1 antibody B2 light chain

<400> SEQUENCE: 4

```
atgacttgga cccccactcct cttcctcacc ctcctcctcc actgcacagg aagcttatcc      60
tcttctgagc tgactcagga ccctgctgtg tcggtggcct tgggacagac agtcacgatc     120
acatgccaag agacagcct caattactat tatgcaaact ggttccagct gaagccaggg     180
caggcccctg tacttgtcct ctttggtaaa acaaccggc cctcagggat cccagaccga     240
ttctctggct cctactcggg aagcacagct tccttgacca tcactggggc tcaggcggaa     300
gatgacgctg actattactg taattcgcgg gacagcggtg gtaatccttg gtgttcggc     360
ggagggacca gctgaccgt cctaggtcaa cccaaggctg ccccctcggt cactctgttc     420
ccgccctcct ctgaggagct tcaagccaac aaggccacac tggtgtgtct cataagtgac     480
ttctacccgg gagccgtgac agtggcctgg aaggcagata gcagcccgt caaggcggga     540
gtggagacca ccacaccctc caaacaaagc aacaacaagt acgcggccag cagctacctg     600
agcctgacgc ctgagcagtg gaagtccac agaagctaca gctgccaggt cacgcatgaa     660
gggagcaccg tggagaagac agtggcccct acagaatgtt catga                    705
```

<210> SEQ ID NO 5
<211> LENGTH: 234
<212> TYPE: PRT
<213> ORGANISM: Artificial Sequence
<220> FEATURE:
<223> OTHER INFORMATION: full length protein sequence of PDL1 antibody B2 light chain

<400> SEQUENCE: 5

```
Met Thr Trp Thr Pro Leu Leu Phe Leu Thr Leu Leu His Cys Thr
1               5                   10                  15
```

```
Gly Ser Leu Ser Ser Glu Leu Thr Gln Asp Pro Ala Val Ser Val
            20                  25                  30

Ala Leu Gly Gln Thr Val Thr Ile Thr Cys Gln Gly Asp Ser Leu Asn
        35                  40                  45

Tyr Tyr Tyr Ala Asn Trp Phe Gln Leu Lys Pro Gly Gln Ala Pro Val
    50                  55                  60

Leu Val Leu Phe Gly Lys Asn Asn Arg Pro Ser Gly Ile Pro Asp Arg
65              70                  75                  80

Phe Ser Gly Ser Tyr Ser Gly Ser Thr Ala Ser Leu Thr Ile Thr Gly
                85                  90                  95

Ala Gln Ala Glu Asp Ala Asp Tyr Tyr Cys Asn Ser Arg Asp Ser
            100                 105                 110

Gly Gly Asn Pro Trp Val Phe Gly Gly Gly Thr Lys Leu Thr Val Leu
            115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Pro Ser Lys Gln Ser Asn Asn
            180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 6
<211> LENGTH: 108
<212> TYPE: PRT
<213> ORGANISM: Artificial Sequence
<220> FEATURE:
<223> OTHER INFORMATION: variable region protein sequence of PDL1
      antibody B2 light chain

<400> SEQUENCE: 6

Ser Ser Glu Leu Thr Gln Asp Pro Ala Val Ser Val Ala Leu Gly Gln
1               5                   10                  15

Thr Val Thr Ile Thr Cys Gln Gly Asp Ser Leu Asn Tyr Tyr Tyr Ala
            20                  25                  30

Asn Trp Phe Gln Leu Lys Pro Gly Gln Ala Pro Val Leu Val Leu Phe
        35                  40                  45

Gly Lys Asn Asn Arg Pro Ser Gly Ile Pro Asp Arg Phe Ser Gly Ser
    50                  55                  60

Tyr Ser Gly Ser Thr Ala Ser Leu Thr Ile Thr Gly Ala Gln Ala Glu
65              70                  75                  80

Asp Asp Ala Asp Tyr Tyr Cys Asn Ser Arg Asp Ser Gly Gly Asn Pro
                85                  90                  95

Trp Val Phe Gly Gly Gly Thr Lys Leu Thr Val Leu
            100                 105

<210> SEQ ID NO 7
<211> LENGTH: 1404
<212> TYPE: DNA
<213> ORGANISM: Artificial Sequence
```

<220> FEATURE:
<223> OTHER INFORMATION: DNA sequence of PDL1 antibody E1 heavy chain

<400> SEQUENCE: 7

| | | |
|---|---|---|
| atggagtttg ggctgagctg gcttttctt gtcgcgattc ttaagggtgt ccagtgccaa | 60 |
| atccagctgg tacaatctgg ggctgaggtg aagatgcctg gggcctcagt gacgatttcc | 120 |
| tgcgaggcgt ctggatacaa cttcatcagc tactatatac actgggtgcg acaggcccct | 180 |
| ggacaaggcc ttgagtggat gggattcgtc gtccctagtg gtggtgccgc aggctacaca | 240 |
| cagaagttcc agggcagact caccgtgacc aggacacgt ccacgagcac agtctacatg | 300 |
| gacctgaaca gcctgacatc tgacgacacg gccgtgtatt actgtgtgcg agaaatgagt | 360 |
| ggtggctggt ttgatttctg gggccaggga accctggtca ccgtctcctc ggcttcgacc | 420 |
| aagggcccat cggtcttccc cctggcaccc tcctccaaga gcacctctgg gggcacagcg | 480 |
| gccctgggct gcctggtcaa ggactacttc cccgaaccgg tgacggtgtc gtggaactca | 540 |
| ggcgccctga ccagcggcgt gcacaccttc ccggctgtcc tacagtcctc aggactctac | 600 |
| tccctcagca gcgtggtgac cgtgccctcc agcagcttgg gcacccagac ctacatctgc | 660 |
| aacgtgaatc acaagcccag caacaccaag gtggacaaga agttgagcc caaatcttgt | 720 |
| gacaaaactc acacatgccc accgtgccca gcacctgaac tcctgggggg accgtcagtc | 780 |
| ttcctcttcc ccccaaaacc caaggacacc ctcatgatct cccggacccc tgaggtcaca | 840 |
| tgcgtggtgg tggacgtgag ccacgaagac cctgaggtca agttcaactg gtacgtggac | 900 |
| ggcgtggagg tgcataatgc caagacaaag ccgcgggagg agcagtacaa cagcacgtac | 960 |
| cgtgtggtca gcgtcctcac cgtcctgcac caggactggc tgaatggcaa ggagtacaag | 1020 |
| tgcaaggtct ccaacaaagc cctcccagcc cccatcgaga aaaccatctc caaagccaaa | 1080 |
| gggcagcccc gagaaccaca ggtgtacacc ctgcccccat cccgcgagga gatgaccaag | 1140 |
| aaccaggtca gcctgacctg cctggtcaaa ggcttctatc ccagcgacat cgccgtggag | 1200 |
| tgggagagca atgggcagcc ggagaacaac tacaagacca cgcctcccgt gctggactcc | 1260 |
| gacggctcct tcttcctcta cagcaagctc accgtggaca agagcaggtg gcagcagggg | 1320 |
| aacgtcttct catgctccgt gatgcatgag gctctgcaca accactacac gcagaagagc | 1380 |
| ctctccctgt ctccgggtaa atga | 1404 |

<210> SEQ ID NO 8
<211> LENGTH: 467
<212> TYPE: PRT
<213> ORGANISM: Artificial Sequence
<220> FEATURE:
<223> OTHER INFORMATION: full length protein sequence of PDL1 antibody
      E1 heavy chain

<400> SEQUENCE: 8

Met Glu Phe Gly Leu Ser Trp Leu Phe Leu Val Ala Ile Leu Lys Gly
1               5                   10                  15

Val Gln Cys Gln Ile Gln Leu Val Gln Ser Gly Ala Glu Val Lys Met
                20                  25                  30

Pro Gly Ala Ser Val Thr Ile Ser Cys Glu Ala Ser Gly Tyr Asn Phe
            35                  40                  45

Ile Ser Tyr Tyr Ile His Trp Val Arg Gln Ala Pro Gly Gln Gly Leu
        50                  55                  60

Glu Trp Met Gly Phe Val Val Pro Ser Gly Gly Ala Ala Gly Tyr Thr
65                  70                  75                  80

```
Gln Lys Phe Gln Gly Arg Leu Thr Val Thr Arg Asp Thr Ser Thr Ser
                85                  90                  95

Thr Val Tyr Met Asp Leu Asn Ser Leu Thr Ser Asp Asp Thr Ala Val
            100                 105                 110

Tyr Tyr Cys Val Arg Glu Met Ser Gly Gly Trp Phe Asp Phe Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 9
<211> LENGTH: 98
<212> TYPE: PRT
```

<213> ORGANISM: Artificial Sequence
<220> FEATURE:
<223> OTHER INFORMATION: variable region protein sequence of PDL1 antibody E1 heavy chain

<400> SEQUENCE: 9

Ser Cys Glu Ala Ser Gly Tyr Asn Phe Ile Ser Tyr Tyr Ile His Trp
1               5                   10                  15

Val Arg Gln Ala Pro Gly Gln Gly Leu Glu Trp Met Gly Phe Val Val
            20                  25                  30

Pro Ser Gly Gly Ala Ala Gly Tyr Thr Gln Lys Phe Gln Gly Arg Leu
        35                  40                  45

Thr Val Thr Arg Asp Thr Ser Thr Ser Thr Val Tyr Met Asp Leu Asn
    50                  55                  60

Ser Leu Thr Ser Asp Asp Thr Ala Val Tyr Tyr Cys Val Arg Glu Met
65                  70                  75                  80

Ser Gly Gly Trp Phe Asp Phe Trp Gly Gln Gly Thr Leu Val Thr Val
                85                  90                  95

Ser Ser

<210> SEQ ID NO 10
<211> LENGTH: 711
<212> TYPE: DNA
<213> ORGANISM: Artificial Sequence
<220> FEATURE:
<223> OTHER INFORMATION: DNA sequence of PDL1 antibody E1 light chain

<400> SEQUENCE: 10
atggacatgc gcgtgcccgc ccagctgctg ggcctgctgc tgctgtggtt ccccggctcg      60
cgatgcgaca tcgtgatgac ccagtctcca tcctcccgt ctgcatctgt aggagacaga     120
gtcaccatca cttgccgggc aagtcagggc attagaaatg atttaggctg gtatcagcaa    180
aaaccaggga aagcccctaa gctcctgatc tatgctgcat ccactttgca aagtggggtc    240
ccatcaaggt tcagcggcag tggatctggg acagatttca ctctcaccat cagcagcctg    300
caggctgaag atgtggcagt ttattactgt cagcaatatt atagtactcc tctcactttc    360
ggccctggga ccaaagtgga tatcaaacgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgttg a             711

<210> SEQ ID NO 11
<211> LENGTH: 236
<212> TYPE: PRT
<213> ORGANISM: Artificial Sequence
<220> FEATURE:
<223> OTHER INFORMATION: full length protein sequence of PDL1 antibody E1 light chain

<400> SEQUENCE: 11

Met Asp Met Arg Val Pro Ala Gln Leu Leu Gly Leu Leu Leu Leu Trp
1               5                   10                  15

Phe Pro Gly Ser Arg Cys Asp Ile Val Met Thr Gln Ser Pro Ser Ser
            20                  25                  30

```
Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
 50                  55                  60

Ala Pro Lys Leu Leu Ile Tyr Ala Ala Ser Thr Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Ala Glu Asp Val Ala Val Tyr Tyr Cys Gln Gln
            100                 105                 110

Tyr Tyr Ser Thr Pro Leu Thr Phe Gly Pro Gly Thr Lys Val Asp Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 12
<211> LENGTH: 107
<212> TYPE: PRT
<213> ORGANISM: Artificial Sequence
<220> FEATURE:
<223> OTHER INFORMATION: variable region protein sequence of PDL1
      antibody E1 light chain

<400> SEQUENCE: 12

Asp Ile Val Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Tyr Ser Thr Pro Leu
                85                  90                  95

Thr Phe Gly Pro Gly Thr Lys Val Asp Ile Lys
            100                 105

<210> SEQ ID NO 13
<211> LENGTH: 1404
<212> TYPE: DNA
<213> ORGANISM: Artificial Sequence
<220> FEATURE:
<223> OTHER INFORMATION: DNA sequence of PDL1 antibody E3 heavy chain
```

<400> SEQUENCE: 13

```
atggagtttg ggctgagctg gcttttctt gtcgcgattc ttaagggtgt ccagtgccaa        60
atccagctgg tacaatctgg ggctgaggtg aagaagcctg gtcctcggt gaaggtctcc       120
tgcaaggctt ctggaggcac cttcagcagc tatgctatca gctgggtgcg acaggcccct      180
ggacaagggc ttgagtggat gggagggatc atccctatct ttggtacagc aaactacgca      240
cagaagttcc agggcagagt cacgattacc gcggacaaat ccacgagcac agcctacatg      300
gagctgagca gcctgagatc tgaggacacg gccgtgtatt actgtgccgg aggggagca       360
gtggcggaca atagttactg gggccaggga accctggtca ccgtctcctc agcttcgacc      420
aagggcccat cggtcttccc cctggcaccc tcctccaaga gcacctctgg gggcacagcg      480
gccctgggct gcctggtcaa ggactacttc cccgaaccgg tgacggtgtc gtggaactca      540
ggcgccctga ccagcggcgt gcacaccttc ccggctgtcc tacagtcctc aggactctac      600
tccctcagca gcgtggtgac cgtgccctcc agcagcttgg gcacccagac ctacatctgc      660
aacgtgaatc acaagcccag caacaccaag gtggacaaga agttgagcc caaatcttgt      720
gacaaaactc acacatgccc accgtgccca gcacctgaac tcctgggggg accgtcagtc      780
ttcctcttcc ccccaaaacc caaggacacc ctcatgatct cccggacccc tgaggtcaca      840
tgcgtggtgg tggacgtgag ccacgaagac cctgaggtca agttcaactg gtacgtggac      900
ggcgtggagg tgcataatgc caagacaaag ccgcgggagg agcagtacaa cagcacgtac      960
cgtgtggtca gcgtcctcac cgtcctgcac caggactggc tgaatggcaa ggagtacaag     1020
tgcaaggtct ccaacaaagc cctcccagcc ccatcgaga aaaccatctc caaagccaaa      1080
gggcagcccc gagaaccaca ggtgtacacc ctgcccccat cccgcgagga gatgaccaag     1140
aaccaggtca gcctgacctg cctggtcaaa ggcttctatc ccagcgacat cgccgtggag     1200
tgggagagca atgggcagcc ggagaacaac tacaagacca cgcctcccgt gctggactcc     1260
gacggctcct tcttcctcta cagcaagctc accgtggaca agagcaggtg gcagcagggg     1320
aacgtcttct catgctccgt gatgcatgag gctctgcaca accactacac gcagaagagc     1380
ctctccctgt ctccgggtaa atga                                            1404
```

<210> SEQ ID NO 14
<211> LENGTH: 467
<212> TYPE: PRT
<213> ORGANISM: Artificial Sequence
<220> FEATURE:
<223> OTHER INFORMATION: full length protein sequence of PDL1 antibody E3 heavy chain

<400> SEQUENCE: 14

```
Met Glu Phe Gly Leu Ser Trp Leu Phe Leu Val Ala Ile Leu Lys Gly
1               5                   10                  15

Val Gln Cys Gln Ile Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Gly Ile Ile Pro Ile Phe Gly Thr Ala Asn Tyr Ala
65                  70                  75                  80

Gln Lys Phe Gln Gly Arg Val Thr Ile Thr Ala Asp Lys Ser Thr Ser
                85                  90                  95
```

Thr Ala Tyr Met Glu Leu Ser Ser Leu Arg Ser Glu Asp Thr Ala Val
            100                 105                 110

Tyr Tyr Cys Ala Gly Gly Ala Val Ala Asp Asn Ser Tyr Trp Gly
            115                 120                 125

Gln Gly Thr Leu Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
            210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465

<210> SEQ ID NO 15
<211> LENGTH: 118
<212> TYPE: PRT
<213> ORGANISM: Artificial Sequence
<220> FEATURE:

<223> OTHER INFORMATION: variable region protein sequence of PDL1
antibody E3 heavy chain

<400> SEQUENCE: 15

Gln Ile Gln Leu Val Gln Ser Gly Ala Glu Val Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Gly Ala Val Ala Asp Asn Ser Tyr Trp Gly Gln Gly Thr
            100                 105                 110

Leu Val Thr Val Ser Ser
        115

<210> SEQ ID NO 16
<211> LENGTH: 711
<212> TYPE: DNA
<213> ORGANISM: Artificial Sequence
<220> FEATURE:
<223> OTHER INFORMATION: DNA sequence of PDL1 antibody E3 light chain

<400> SEQUENCE: 16
atggacatgc gcgtgcccgc ccagctgctg ggcctgctgc tgctgtggtt ccccggctcg        60
cgatgcgaca tccggatgac ccagtctcca tcctccctgt ctgcatctgt aggagacaga       120
gtcaccatca cttgccgggc aagtcagggc attagaaatg atttaggctg gtatcagcag       180
aaaccaggga agcccctaa gctcctgatc tatgctgcat ccagtttaca agtggggtc        240 ccatcaaggt tcagcggcag tggatctggc acagatttca ctctcaccat cagcagcctg       300
cagcctgaag attttgcaac ttattactgt ctacaagatt acaattaccc tcgaacgttc       360
ggccaaggga ccaaggtgga aatcaaacgt acggtggctg caccatctgt cttcatcttc       420
ccgccatctg atgagcagtt gaaatctgga actgcctctg ttgtgtgcct gctgaataac       480
ttctatccca gagaggccaa agtacagtgg aaggtggata acgccctcca atcgggtaac       540
tcccaggaga gtgtcacaga gcaggacagc aaggacagca cctacagcct cagcagcacc       600
ctgacgctga gcaaagcaga ctacgagaaa cacaaagtct acgcctgcga agtcacccat       660
cagggcctga gctcgcccgt cacaaagagc ttcaacaggg gagagtgttg a                711

<210> SEQ ID NO 17
<211> LENGTH: 236
<212> TYPE: PRT
<213> ORGANISM: Artificial Sequence
<220> FEATURE:
<223> OTHER INFORMATION: full length protein sequence of PDL1 antibody
E3 light chain

<400> SEQUENCE: 17

Met Asp Met Arg Val Pro Ala Gln Leu Leu Gly Leu Leu Leu Leu Trp
1               5                   10                  15

Phe Pro Gly Ser Arg Cys Asp Ile Arg Met Thr Gln Ser Pro Ser Ser
            20                  25                  30

```
Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
 50                  55                  60

Ala Pro Lys Leu Leu Ile Tyr Ala Ala Ser Ser Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Leu Gln
                100                 105                 110

Asp Tyr Asn Tyr Pro Arg Thr Phe Gly Gln Gly Thr Lys Val Glu Ile
                115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 18
<211> LENGTH: 107
<212> TYPE: PRT
<213> ORGANISM: Artificial Sequence
<220> FEATURE:
<223> OTHER INFORMATION: variable region protein sequence of PDL1
      antibody E3 light chain

<400> SEQUENCE: 18

Asp Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Arg
                85                  90                  95

Thr Phe Gly Gln Gly Thr Lys Val Glu Ile Lys
                100                 105

<210> SEQ ID NO 19
<211> LENGTH: 20
<212> TYPE: PRT
<213> ORGANISM: Artificial Sequence
<220> FEATURE:
<223> OTHER INFORMATION: Ser-Gly linker
```

<400> SEQUENCE: 19

Gly Gly Gly Gly Ser Gly Gly Gly Ser Gly Gly Gly Gly Ser Gly
1               5                   10                  15

Gly Gly Gly Ser
            20

<210> SEQ ID NO 20
<211> LENGTH: 405
<212> TYPE: DNA
<213> ORGANISM: Artificial Sequence
<220> FEATURE:
<223> OTHER INFORMATION: IL2WT DNA sequence

<400> SEQUENCE: 20

```
ggcgccccca catcctccag caccaagaag acccagctgc agctggagca tctgctgctg      60
gatctgcaga tgattttaaa cggcatcaac aactacaaga accccaagct gacccggatg     120
ctgaccttca gttctacat gcccaagaag gccaccgagc tgaagcattt acagtgtctg      180
gaggaagagc tgaagccttt agaggaagtg ctcaatttag cccagtccaa gaacttccat     240
ttaaggccac gtgatttaat ctccaacatc aacgtgatcg tgctggagct gaagggctcc     300
gagaccacct tcatgtgcga gtacgccgac gagaccgcca ccatcgtgga gttttaaat     360
cgttggatca ccttctgcca gagcatcatc tccactttaa cctga                     405
```

<210> SEQ ID NO 21
<211> LENGTH: 134
<212> TYPE: PRT
<213> ORGANISM: Artificial Sequence
<220> FEATURE:
<223> OTHER INFORMATION: IL2WT protein sequence

<400> SEQUENCE: 21

Gly Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130

<210> SEQ ID NO 22
<211> LENGTH: 345
<212> TYPE: DNA
<213> ORGANISM: Artificial Sequence
<220> FEATURE:
<223> OTHER INFORMATION: IL2Del DNA sequence

<400> SEQUENCE: 22

```
ggcgccccca catcctccag caccaagaag acccagctgc agctggagca tctgctgctg    60
gatctgcaga tgattttaaa cggcatcaac gccaccgagc tgaagcattt acagtgtctg   120
gaggaagagc tgaagccttt agaggaagtg ctcaatttag cccagtccaa gaacttccat   180
ttaaggccac gtgatttaat ctccaacatc aacgtgatcg tgctggagct gaagggctcc   240
gagaccacct tcatgtgcga gtacgccgac gagaccgcca ccatcgtgga gttttttaaat   300
cgttggatca ccttctgcca gagcatcatc tccactttaa cctga                   345
```

```
<210> SEQ ID NO 23
<211> LENGTH: 114
<212> TYPE: PRT
<213> ORGANISM: Artificial Sequence
<220> FEATURE:
<223> OTHER INFORMATION: IL2Del protein sequence
```

<400> SEQUENCE: 23

```
Gly Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Ala Thr
            20                  25                  30

Glu Leu Lys His Leu Gln Cys Leu Glu Glu Glu Leu Lys Pro Leu Glu
        35                  40                  45

Glu Val Leu Asn Leu Ala Gln Ser Lys Asn Phe His Leu Arg Pro Arg
    50                  55                  60

Asp Leu Ile Ser Asn Ile Asn Val Ile Val Leu Glu Leu Lys Gly Ser
65                  70                  75                  80

Glu Thr Thr Phe Met Cys Glu Tyr Ala Asp Glu Thr Ala Thr Ile Val
                85                  90                  95

Glu Phe Leu Asn Arg Trp Ile Thr Phe Cys Gln Ser Ile Ile Ser Thr
            100                 105                 110

Leu Thr
```

```
<210> SEQ ID NO 24
<211> LENGTH: 405
<212> TYPE: DNA
<213> ORGANISM: Artificial Sequence
<220> FEATURE:
<223> OTHER INFORMATION: IL2M1: F42K, Y45R DNA sequence
```

<400> SEQUENCE: 24

```
ggcgccccca catcctccag caccaagaag acccagctgc agctggagca tctgctgctg    60
gatctgcaga tgattttaaa cggcatcaac aactacaaga accccaagct gacccggatg   120
ctgaccaaga agttccgcat gcccaagaag gccaccgagc tgaagcattt acagtgtctg   180
gaggaagagc tgaagccttt agaggaagtg ctcaatttag cccagtccaa gaacttccat   240
ttaaggccac gtgatttaat ctccaacatc aacgtgatcg tgctggagct gaagggctcc   300
gagaccacct tcatgtgcga gtacgccgac gagaccgcca ccatcgtgga gttttttaaat   360
cgttggatca ccttctgcca gagcatcatc tccactttaa cctga                   405
```

```
<210> SEQ ID NO 25
<211> LENGTH: 134
<212> TYPE: PRT
<213> ORGANISM: Artificial Sequence
<220> FEATURE:
<223> OTHER INFORMATION: IL2M1: F42K, Y45R protein sequence
```

<400> SEQUENCE: 25

Gly Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Lys Lys Phe Arg Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
            130

<210> SEQ ID NO 26
<211> LENGTH: 405
<212> TYPE: DNA
<213> ORGANISM: Artificial Sequence
<220> FEATURE:
<223> OTHER INFORMATION: IL2M2: F42A, Y45R DNA sequence

<400> SEQUENCE: 26
ggcgccccca catcctccag caccaagaag acccagctgc agctggagca tctgctgctg      60
gatctgcaga tgattttaaa cggcatcaac aactacaaga ccccaagct gacccggatg     120
ctgaccgcca agttccgcat gcccaagaag gccaccgagc tgaagcattt acagtgtctg    180
gaggaagagc tgaagccttt agaggaagtg ctcaatttag cccagtccaa gaacttccat    240
ttaaggccac gtgatttaat ctccaacatc aacgtgatcg tgctggagct gaagggctcc    300
gagaccacct tcatgtgcga gtacgccgac gagaccgcca ccatcgtgga gttttttaaat    360
cgttggatca ccttctgcca gagcatcatc tccactttaa cctga                     405

<210> SEQ ID NO 27
<211> LENGTH: 134
<212> TYPE: PRT
<213> ORGANISM: Artificial Sequence
<220> FEATURE:
<223> OTHER INFORMATION: IL2M2: F42A, Y45R protein sequence

<400> SEQUENCE: 27

Gly Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Ala Lys Phe Arg Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130

<210> SEQ ID NO 28
<211> LENGTH: 405
<212> TYPE: DNA
<213> ORGANISM: Artificial Sequence
<220> FEATURE:
<223> OTHER INFORMATION: IL2M3: E62R DNA sequence

<400> SEQUENCE: 28
ggcgccccca catcctccag caccaagaag acccagctgc agctggagca tctgctgctg      60
gatctgcaga tgattttaaa cggcatcaac aactacaaga cccccaagct gacccggatg     120
ctgaccttca agttctacat gcccaagaag gccaccgagc tgaagcattt acagtgtctg     180
gaggaaaggc tgaagccttt agaggaagtg ctcaatttag cccagtccaa gaacttccat     240
ttaaggccac gtgatttaat ctccaacatc aacgtgatcg tgctggagct gaagggctcc     300
gagaccacct tcatgtgcga gtacgccgac gagaccgcca ccatcgtgga gttttaaat     360 cgttggatca ccttctgcca gagcatcatc tccactttaa cctga                    405

<210> SEQ ID NO 29
<211> LENGTH: 134
<212> TYPE: PRT
<213> ORGANISM: Artificial Sequence
<220> FEATURE:
<223> OTHER INFORMATION: IL2M3: E62R protein sequence

<400> SEQUENCE: 29

Gly Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Arg Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130

<210> SEQ ID NO 30
<211> LENGTH: 405
<212> TYPE: DNA
<213> ORGANISM: Artificial Sequence
<220> FEATURE:

<223> OTHER INFORMATION: IL2M4: R38A, F42A DNA sequence

<400> SEQUENCE: 30

| ggcgccccca | catcctccag | caccaagaag | acccagctgc | agctggagca | tctgctgctg | 60 |
| gatctgcaga | tgatttttaaa | cggcatcaac | aactacaaga | accccaagct | gaccgccatg | 120 |
| ctgaccgcca | agttctacat | gcccaagaag | gccaccgagc | tgaagcattt | acagtgtctg | 180 |
| gaggaagagc | tgaagccttt | agaggaagtg | ctcaatttag | cccagtccaa | gaacttccat | 240 |
| ttaaggccac | gtgatttaat | ctccaacatc | aacgtgatcg | tgctggagct | gaagggctcc | 300 |
| gagaccacct | tcatgtgcga | gtacgccgac | gagaccgcca | ccatcgtgga | gttttttaaat | 360 |
| cgttggatca | ccttctgcca | gagcatcatc | tccactttaa | cctga | | 405 |

<210> SEQ ID NO 31
<211> LENGTH: 134
<212> TYPE: PRT
<213> ORGANISM: Artificial Sequence
<220> FEATURE:
<223> OTHER INFORMATION: IL2M4: R38A, F42A protein sequence

<400> SEQUENCE: 31

Gly Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Ala Met Leu Thr Ala Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130

<210> SEQ ID NO 32
<211> LENGTH: 405
<212> TYPE: DNA
<213> ORGANISM: Artificial Sequence
<220> FEATURE:
<223> OTHER INFORMATION: IL2M5: R38A, F42A, Y45A, E62A, C125S DNA
      sequence

<400> SEQUENCE: 32

| ggagctccta | cctcctcctc | caccaagaag | acccagctcc | agctggaaca | tttactgctg | 60 |
| gatttacaga | tgatttttaaa | cggcatcaac | aattacaaga | accccaagct | gaccgccatg | 120 |
| ctgaccgcca | agtttgccat | gcccaagaag | gccaccgagc | tgaagcattt | acagtgttta | 180 |
| gaggaggctt | taaagccttt | agaggaggtg | ctgaatttag | cccagtccaa | gaacttccat | 240 |
| ttaaggcccc | gggatttaat | ctccaacatc | aacgtgatcg | tgctggaact | gaagggcagc | 300 |
| gagaccacct | ttatgagcga | atacgccgac | gagaccgcca | ccatcgtgga | gttttttaaat | 360 |
| cgttggatca | ccttctgcca | gtccatcatc | tccactttaa | cctga | | 405 |

<210> SEQ ID NO 33
<211> LENGTH: 134
<212> TYPE: PRT
<213> ORGANISM: Artificial Sequence
<220> FEATURE:
<223> OTHER INFORMATION: IL2M5: R38A, F42A, Y45A, E62A, C125S protein sequence

<400> SEQUENCE: 33

Gly Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Ala Met Leu Thr Ala Lys Phe Ala Met Pro
        35                  40                  45

Lys Lys Ala Thr Glu Leu Lys His Leu Gln Cys Leu Glu Glu Ala Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Ser Glu Tyr Ala Asp Glu Thr
            100                 105                 110

Ala Thr Ile Val Glu Phe Leu Asn Arg Trp Ile Thr Phe Ser Gln Ser
        115                 120                 125

Ile Ile Ser Thr Leu Thr
    130

<210> SEQ ID NO 34
<211> LENGTH: 405
<212> TYPE: DNA
<213> ORGANISM: Artificial Sequence
<220> FEATURE:
<223> OTHER INFORMATION: IL2M6: R38A, F42K DNA sequence

<400> SEQUENCE: 34
ggcgccccca catcctccag caccaagaag acccagctgc agctggagca tctgctgctg      60
gatctgcaga tgattttaaa cggcatcaac aactacaaga accccaagct gaccgccatg     120
ctgaccaaga agttctacat gcccaagaag gccaccgagc tgaagcattt acagtgtctg     180
gaggaagagc tgaagccttt agaggaagtg ctcaatttag cccagtccaa gaacttccat     240
ttaaggccac gtgatttaat ctccaacatc aacgtgatcg tgctggagct gaagggctcc     300
gagaccacct tcatgtgcga gtacgccgac gagaccgcca ccatcgtgga gttttttaaat     360 cgttggatca ccttctgcca gagcatcatc tccactttaa cctga                     405

<210> SEQ ID NO 35
<211> LENGTH: 134
<212> TYPE: PRT
<213> ORGANISM: Artificial Sequence
<220> FEATURE:
<223> OTHER INFORMATION: IL2M6: R38A, F42K protein sequence

<400> SEQUENCE: 35

Gly Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Ala Met Leu Thr Lys Lys Phe Tyr Met Pro
                35                  40                  45

Lys Lys Ala Thr Glu Leu Lys His Leu Gln Cys Leu Glu Glu Glu Leu
 50                  55                  60

Lys Pro Leu Glu Glu Val Leu Asn Leu Ala Gln Ser Lys Asn Phe His
 65                  70                  75                  80

Leu Arg Pro Arg Asp Leu Ile Ser Asn Ile Asn Val Ile Val Leu Glu
                 85                  90                  95

Leu Lys Gly Ser Glu Thr Thr Phe Met Cys Glu Tyr Ala Asp Glu Thr
                100                 105                 110

Ala Thr Ile Val Glu Phe Leu Asn Arg Trp Ile Thr Phe Cys Gln Ser
                115                 120                 125

Ile Ile Ser Thr Leu Thr
            130

<210> SEQ ID NO 36
<211> LENGTH: 405
<212> TYPE: DNA
<213> ORGANISM: Artificial Sequence
<220> FEATURE:
<223> OTHER INFORMATION: IL2M7: R38A, F42A, E62R DNA sequence

<400> SEQUENCE: 36
ggcgccccca catcctccag caccaagaag acccagctgc agctggagca tctgctgctg      60
gatctgcaga tgattttaaa cggcatcaac aactacaaga cccccaagct gaccgccatg     120
ctgaccgcca agttctacat gcccaagaag gccaccgagc tgaagcattt acagtgtctg     180
gaggaaaggc tgaagccttt agaggaagtg ctcaatttag cccagtccaa gaacttccat     240
ttaaggccac gtgatttaat ctccaacatc aacgtgatcg tgctggagct gaagggctcc     300
gagaccacct tcatgtgcga gtacgccgac gagaccgcca ccatcgtgga gttttttaaat    360 cgttggatca ccttctgcca gagcatcatc tccactttaa cctga                     405

<210> SEQ ID NO 37
<211> LENGTH: 134
<212> TYPE: PRT
<213> ORGANISM: Artificial Sequence
<220> FEATURE:
<223> OTHER INFORMATION: IL2M7: R38A, F42A, E62R Protein sequence

<400> SEQUENCE: 37

Gly Ala Pro Thr Ser Ser Ser Thr Lys Lys Thr Gln Leu Gln Leu Glu
 1               5                  10                  15

His Leu Leu Leu Asp Leu Gln Met Ile Leu Asn Gly Ile Asn Asn Tyr
                20                  25                  30

Lys Asn Pro Lys Leu Thr Ala Met Leu Thr Ala Lys Phe Tyr Met Pro
                35                  40                  45

Lys Lys Ala Thr Glu Leu Lys His Leu Gln Cys Leu Glu Glu Arg Leu
 50                  55                  60

Lys Pro Leu Glu Glu Val Leu Asn Leu Ala Gln Ser Lys Asn Phe His
 65                  70                  75                  80

Leu Arg Pro Arg Asp Leu Ile Ser Asn Ile Asn Val Ile Val Leu Glu
                 85                  90                  95

Leu Lys Gly Ser Glu Thr Thr Phe Met Cys Glu Tyr Ala Asp Glu Thr
                100                 105                 110

Ala Thr Ile Val Glu Phe Leu Asn Arg Trp Ile Thr Phe Cys Gln Ser
                115                 120                 125

-continued

```
Ile Ile Ser Thr Leu Thr
    130
```

<210> SEQ ID NO 38
<211> LENGTH: 405
<212> TYPE: DNA
<213> ORGANISM: Artificial Sequence
<220> FEATURE:
<223> OTHER INFORMATION: IL2M8: F42K, Y45R, E62R DNA sequence

<400> SEQUENCE: 38

```
ggcgccccca catcctccag caccaagaag acccagctgc agctggagca tctgctgctg    60
gatctgcaga tgattttaaa cggcatcaac aactacaaga accccaagct gacccggatg   120
ctgaccaaga agttccgcat gcccaagaag gccaccgagc tgaagcattt acagtgtctg   180
gaggaaaggc tgaagccttt agaggaagtg ctcaatttag cccagtccaa gaacttccat   240
ttaaggccac gtgattaat ctccaacatc aacgtgatcg tgctggagct gaagggctcc   300
gagaccacct tcatgtgcga gtacgccgac gagaccgcca ccatcgtgga gttttaaat   360
cgttggatca ccttctgcca gagcatcatc tccactttaa cctga                  405
```

<210> SEQ ID NO 39
<211> LENGTH: 134
<212> TYPE: PRT
<213> ORGANISM: Artificial Sequence
<220> FEATURE:
<223> OTHER INFORMATION: IL2M8: F42K, Y45R, E62R Protein sequence

<400> SEQUENCE: 39

```
Gly Ala Pro Thr Ser Ser Ser Thr Lys Lys Thr Gln Leu Gln Leu Glu
1               5                   10                  15
His Leu Leu Leu Asp Leu Gln Met Ile Leu Asn Gly Ile Asn Asn Tyr
            20                  25                  30
Lys Asn Pro Lys Leu Thr Arg Met Leu Thr Lys Lys Phe Arg Met Pro
        35                  40                  45
Lys Lys Ala Thr Glu Leu Lys His Leu Gln Cys Leu Glu Glu Arg Leu
    50                  55                  60
Lys Pro Leu Glu Glu Val Leu Asn Leu Ala Gln Ser Lys Asn Phe His
65                  70                  75                  80
Leu Arg Pro Arg Asp Leu Ile Ser Asn Ile Asn Val Ile Val Leu Glu
                85                  90                  95
Leu Lys Gly Ser Glu Thr Thr Phe Met Cys Glu Tyr Ala Asp Glu Thr
            100                 105                 110
Ala Thr Ile Val Glu Phe Leu Asn Arg Trp Ile Thr Phe Cys Gln Ser
        115                 120                 125
Ile Ile Ser Thr Leu Thr
    130
```

<210> SEQ ID NO 40
<211> LENGTH: 405
<212> TYPE: DNA
<213> ORGANISM: Artificial Sequence
<220> FEATURE:
<223> OTHER INFORMATION: IL2M9: F42A, Y45R, E62R DNA sequence

<400> SEQUENCE: 40

```
ggcgccccca catcctccag caccaagaag acccagctgc agctggagca tctgctgctg    60
gatctgcaga tgattttaaa cggcatcaac aactacaaga accccaagct gacccggatg   120
ctgaccgcca agttccgcat gcccaagaag gccaccgagc tgaagcattt acagtgtctg   180
```

```
gaggaaaggc tgaagccttt agaggaagtg ctcaatttag cccagtccaa gaacttccat    240
ttaaggccac gtgatttaat ctccaacatc aacgtgatcg tgctggagct gaagggctcc    300
gagaccacct tcatgtgcga gtacgccgac gagaccgcca ccatcgtgga gttttttaaat   360 cgttggatca ccttctgcca gagcatcatc tccactttaa cctga                    405
```

```
<210> SEQ ID NO 41
<211> LENGTH: 134
<212> TYPE: PRT
<213> ORGANISM: Artificial Sequence
<220> FEATURE:
<223> OTHER INFORMATION: IL2M9: F42A, Y45R, E62R Protein sequence

<400> SEQUENCE: 41
```

Gly Ala Pro Thr Ser Ser Ser Thr Lys Lys Thr Gln Leu Gln Leu Glu
 1               5                  10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Ala Lys Phe Arg Met Pro
        35                  40                  45

Lys Lys Ala Thr Glu Leu Lys His Leu Gln Cys Leu Glu Glu Arg Leu
50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
        130

```
<210> SEQ ID NO 42
<211> LENGTH: 405
<212> TYPE: DNA
<213> ORGANISM: Artificial Sequence
<220> FEATURE:
<223> OTHER INFORMATION: IL2M10: R38A, F42K, E62R DNA sequence
<400> SEQUENCE: 42
ggcgccccca catcctccag caccaagaag acccagctgc agctggagca tctgctgctg     60
gatctgcaga tgattttaaa cggcatcaac aactacaaga cccccaagct gaccgccatg    120
ctgaccaaga agttctacat gcccaagaag gccaccgagc tgaagcattt acagtgtctg    180
gaggaaaggc tgaagccttt agaggaagtg ctcaatttag cccagtccaa gaacttccat    240
ttaaggccac gtgatttaat ctccaacatc aacgtgatcg tgctggagct gaagggctcc    300
gagaccacct tcatgtgcga gtacgccgac gagaccgcca ccatcgtgga gttttttaaat   360 cgttggatca ccttctgcca gagcatcatc tccactttaa cctga                    405
```

```
<210> SEQ ID NO 43
<211> LENGTH: 134
<212> TYPE: PRT
<213> ORGANISM: Artificial Sequence
<220> FEATURE:
<223> OTHER INFORMATION: IL2M10: R38A, F42K, E62R Protein sequence
```

<400> SEQUENCE: 43

Gly Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Ala Met Leu Thr Lys Lys Phe Tyr Met Pro
        35                  40                  45

Lys Lys Ala Thr Glu Leu Lys His Leu Gln Cys Leu Glu Glu Arg Leu
50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
        130

<210> SEQ ID NO 44
<211> LENGTH: 345
<212> TYPE: DNA
<213> ORGANISM: Artificial Sequence
<220> FEATURE:
<223> OTHER INFORMATION: IL2DelM3: Del, E62R DNA sequence

<400> SEQUENCE: 44
ggcgccccca catcctccag caccaagaag acccagctgc agctggagca tctgctgctg      60
gatctgcaga tgattttaaa cggcatcaac gccaccgagc tgaagcattt acagtgtctg     120
gaggaaaggc tgaagccttt agaggaagtg ctcaatttag cccagtccaa gaacttccat     180
ttaaggccac gtgatttaat ctccaacatc aacgtgatcg tgctggagct gaagggctcc     240
gagaccacct tcatgtgcga gtacgccgac gagaccgcca ccatcgtgga gttttttaaat     300
cgttggatca ccttctgcca gagcatcatc tccactttaa cctga                    345

<210> SEQ ID NO 45
<211> LENGTH: 114
<212> TYPE: PRT
<213> ORGANISM: Artificial Sequence
<220> FEATURE:
<223> OTHER INFORMATION: IL2DelM3: Del, E62R Protein sequence

<400> SEQUENCE: 45

Gly Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Ala Thr
            20                  25                  30

Glu Leu Lys His Leu Gln Cys Leu Glu Glu Arg Leu Lys Pro Leu Glu
        35                  40                  45

Glu Val Leu Asn Leu Ala Gln Ser Lys Asn Phe His Leu Arg Pro Arg
50                  55                  60

Asp Leu Ile Ser Asn Ile Asn Val Ile Val Leu Glu Leu Lys Gly Ser
65                  70                  75                  80

Glu Thr Thr Phe Met Cys Glu Tyr Ala Asp Glu Thr Ala Thr Ile Val
            85                  90                  95

Glu Phe Leu Asn Arg Trp Ile Thr Phe Cys Gln Ser Ile Ile Ser Thr
                100                 105                 110

Leu Thr

<210> SEQ ID NO 46
<211> LENGTH: 405
<212> TYPE: DNA
<213> ORGANISM: Artificial Sequence
<220> FEATURE:
<223> OTHER INFORMATION: IL2M3K: E62K DNA sequence

<400> SEQUENCE: 46
ggcgccccca catcctccag caccaagaag acccagctgc agctggagca tctgctgctg      60
gatctgcaga tgattttaaa cggcatcaac aactacaaga accccaagct gacccggatg     120
ctgaccttca agttctacat gcccaagaag gccaccgagc tgaagcattt acagtgtctg     180
gaggaaaagc tgaagccttt agaggaagtg ctcaatttag cccagtccaa gaacttccat     240
ttaaggccac gtgatttaat ctccaacatc aacgtgatcg tgctggagct gaagggctcc     300
gagaccacct tcatgtgcga gtacgccgac gagaccgcca ccatcgtgga gttttaaat      360 cgttggatca ccttctgcca gagcatcatc tccactttaa cctga                     405

<210> SEQ ID NO 47
<211> LENGTH: 134
<212> TYPE: PRT
<213> ORGANISM: Artificial Sequence
<220> FEATURE:
<223> OTHER INFORMATION: IL2M3K: E62K Protein sequence

<400> SEQUENCE: 47

Gly Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Lys Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130

<210> SEQ ID NO 48
<211> LENGTH: 405
<212> TYPE: DNA
<213> ORGANISM: Artificial Sequence
<220> FEATURE:
<223> OTHER INFORMATION: IL2M6K: R38A, F42K, E62K DNA sequence

```
<400> SEQUENCE: 48
ggcgccccca catcctccag caccaagaag acccagctgc agctggagca tctgctgctg    60
gatctgcaga tgattttaaa cggcatcaac aactacaaga accccaagct gaccgccatg   120
ctgaccaaga agttctacat gcccaagaag gccaccgagc tgaagcattt acagtgtctg   180
gaggaaaagc tgaagccttt agaggaagtg ctcaatttag cccagtccaa gaacttccat   240
ttaaggccac gtgatttaat ctccaacatc aacgtgatcg tgctggagct gaagggctcc   300
gagaccacct tcatgtgcga gtacgccgac gagaccgcca ccatcgtgga gttttaaat   360 cgttggatca ccttctgcca gagcatcatc tccactttaa cctga               405

<210> SEQ ID NO 49
<211> LENGTH: 134
<212> TYPE: PRT
<213> ORGANISM: Artificial Sequence
<220> FEATURE:
<223> OTHER INFORMATION: IL2M6K: R38A, F42K, E62K Protein sequence

<400> SEQUENCE: 49

Gly Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Ala Met Leu Thr Lys Lys Phe Tyr Met Pro
        35                  40                  45

Lys Lys Ala Thr Glu Leu Lys His Leu Gln Cys Leu Glu Glu Lys Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130

<210> SEQ ID NO 50
<211> LENGTH: 405
<212> TYPE: DNA
<213> ORGANISM: Artificial Sequence
<220> FEATURE:
<223> OTHER INFORMATION: IL2M7K: R38A, F42A, E62K DNA sequence

<400> SEQUENCE: 50
ggcgccccca catcctccag caccaagaag acccagctgc agctggagca tctgctgctg    60
gatctgcaga tgattttaaa cggcatcaac aactacaaga accccaagct gaccgccatg   120
ctgaccgcca agttctacat gcccaagaag gccaccgagc tgaagcattt acagtgtctg   180
gaggaaaagc tgaagccttt agaggaagtg ctcaatttag cccagtccaa gaacttccat   240
ttaaggccac gtgatttaat ctccaacatc aacgtgatcg tgctggagct gaagggctcc   300
gagaccacct tcatgtgcga gtacgccgac gagaccgcca ccatcgtgga gttttaaat   360 cgttggatca ccttctgcca gagcatcatc tccactttaa cctga               405
```

```
<210> SEQ ID NO 51
<211> LENGTH: 134
<212> TYPE: PRT
<213> ORGANISM: Artificial Sequence
<220> FEATURE:
<223> OTHER INFORMATION: IL2M7K: R38A, F42A, E62K Protein sequence

<400> SEQUENCE: 51

Gly Ala Pro Thr Ser Ser Ser Thr Lys Lys Thr Gln Leu Gln Leu Glu
1               5                   10                  15

His Leu Leu Asp Leu Gln Met Ile Leu Asn Gly Ile Asn Asn Tyr
            20                  25                  30

Lys Asn Pro Lys Leu Thr Ala Met Leu Thr Ala Lys Phe Tyr Met Pro
        35                  40                  45

Lys Lys Ala Thr Glu Leu Lys His Leu Gln Cys Leu Glu Glu Lys Leu
50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130

<210> SEQ ID NO 52
<211> LENGTH: 405
<212> TYPE: DNA
<213> ORGANISM: Artificial Sequence
<220> FEATURE:
<223> OTHER INFORMATION: IL2M8K: F42K, Y45R, E62K DNA sequence

<400> SEQUENCE: 52
ggcgccccca catcctccag caccaagaag acccagctgc agctggagca tctgctgctg      60
gatctgcaga tgattttaaa cggcatcaac aactacaaga acccaagct gacccggatg     120 ctgaccaaga agttccgcat gcccaagaag gccaccgagc tgaagcattt acagtgtctg    180
gaggaaaagc tgaagccttt agaggaagtg ctcaatttag cccagtccaa gaacttccat    240
ttaaggccac gtgatttaat ctccaacatc aacgtgatcg tgctggagct gaagggctcc    300
gagaccacct tcatgtgcga gtacgccgac gagaccgcca ccatcgtgga gttttaaat    360 cgttggatca ccttctgcca gagcatcatc tccactttaa cctga                    405

<210> SEQ ID NO 53
<211> LENGTH: 134
<212> TYPE: PRT
<213> ORGANISM: Artificial Sequence
<220> FEATURE:
<223> OTHER INFORMATION: IL2M8K: F42K, Y45R, E62K Protein sequence

<400> SEQUENCE: 53

Gly Ala Pro Thr Ser Ser Ser Thr Lys Lys Thr Gln Leu Gln Leu Glu
1               5                   10                  15

His Leu Leu Asp Leu Gln Met Ile Leu Asn Gly Ile Asn Asn Tyr
            20                  25                  30

Lys Asn Pro Lys Leu Thr Arg Met Leu Thr Lys Lys Phe Arg Met Pro
        35                  40                  45
```

Lys Lys Ala Thr Glu Leu Lys His Leu Gln Cys Leu Glu Glu Lys Leu
         50                  55                  60

Lys Pro Leu Glu Glu Val Leu Asn Leu Ala Gln Ser Lys Asn Phe His
 65                  70                  75                  80

Leu Arg Pro Arg Asp Leu Ile Ser Asn Ile Asn Val Ile Val Leu Glu
                 85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130

<210> SEQ ID NO 54
<211> LENGTH: 405
<212> TYPE: DNA
<213> ORGANISM: Artificial Sequence
<220> FEATURE:
<223> OTHER INFORMATION: IL2M9K: F42A, Y45R, E62K DNA sequence

<400> SEQUENCE: 54
ggcgccccca catcctccag caccaagaag acccagctgc agctggagca tctgctgctg     60
gatctgcaga tgattttaaa cggcatcaac aactacaaga accccaagct gacccggatg    120
ctgaccgcca agttccgcat gcccaagaag gccaccgagc tgaagcattt acagtgtctg    180
gaggaaaagc tgaagccttt agaggaagtg ctcaatttag cccagtccaa gaacttccat    240
ttaaggccac gtgatttaat ctccaacatc aacgtgatcg tgctggagct gaagggctcc    300
gagaccacct tcatgtgcga gtacgccgac gagaccgcca ccatcgtgga gttttaaat    360 cgttggatca ccttctgcca gagcatcatc tccactttaa cctga                    405

<210> SEQ ID NO 55
<211> LENGTH: 134
<212> TYPE: PRT
<213> ORGANISM: Artificial Sequence
<220> FEATURE:
<223> OTHER INFORMATION: IL2M9K: F42A, Y45R, E62K Protein sequence

<400> SEQUENCE: 55

Gly Ala Pro Thr Ser Ser Ser Thr Lys Lys Thr Gln Leu Gln Leu Glu
 1               5                  10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Ala Lys Phe Arg Met Pro
        35                  40                  45

Lys Lys Ala Thr Glu Leu Lys His Leu Gln Cys Leu Glu Glu Lys Leu
 50                  55                  60

Lys Pro Leu Glu Glu Val Leu Asn Leu Ala Gln Ser Lys Asn Phe His
 65                  70                  75                  80

Leu Arg Pro Arg Asp Leu Ile Ser Asn Ile Asn Val Ile Val Leu Glu
                 85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130

<210> SEQ ID NO 56
<211> LENGTH: 405
<212> TYPE: DNA
<213> ORGANISM: Artificial Sequence
<220> FEATURE:
<223> OTHER INFORMATION: IL2MNew: K35E R38A F42A E61K L72G DNA sequence

<400> SEQUENCE: 56

```
ggcgccccca catcctccag caccaagaag acccagctgc agctggagca tctgctgctg      60
gatctgcaga tgattttaaa cggcatcaac aactacaaga accccgagct gaccgccatg     120
ctgaccgcca agttctacat gcccaagaag gccaccgagc tgaagcattt acagtgtctg     180
gagaaagagc tgaagccttt agaggaagtg ctcaatggcg cccagtccaa gaacttccat     240
ttaaggccac gtgatttaat ctccaacatc aacgtgatcg tgctggagct gaagggctcc     300
gagaccacct tcatgtgcga gtacgccgac gagaccgcca ccatcgtgga gttttaaat     360 cgttggatca ccttctgcca gagcatcatc tccactttaa cctga                   405
```

<210> SEQ ID NO 57
<211> LENGTH: 134
<212> TYPE: PRT
<213> ORGANISM: Artificial Sequence
<220> FEATURE:
<223> OTHER INFORMATION: IL2MNew: K35E R38A F42A E61K L72G Protein sequence

<400> SEQUENCE: 57

```
Gly Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Glu Leu Thr Ala Met Leu Thr Ala Lys Phe Tyr Met Pro
        35                  40                  45

Lys Lys Ala Thr Glu Leu Lys His Leu Gln Cys Leu Glu Lys Glu Leu
    50                  55                  60

Lys Pro Leu Glu Glu Val Leu Asn Gly Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130
```